United States Patent
Olson et al.

(10) Patent No.: US 11,364,366 B2
(45) Date of Patent: Jun. 21, 2022

(54) EXTERNAL CATHETER STABILIZER

(71) Applicant: Olson, Sarah L., Hugo, MN (US)

(72) Inventors: Sarah L. Olson, Hugo, MN (US); Frank Melendez, Doral, FL (US)

(73) Assignee: LEVITY PRODUCTS, INC., Mahtomedi, MN (US)

( * ) Notice: Subject to any disclaimer, the term of this patent is extended or adjusted under 35 U.S.C. 154(b) by 93 days.

(21) Appl. No.: 16/722,700

(22) Filed: Dec. 20, 2019

(65) Prior Publication Data
US 2020/0206468 A1    Jul. 2, 2020

Related U.S. Application Data

(60) Provisional application No. 62/826,057, filed on Mar. 29, 2019, provisional application No. 62/783,385, filed on Dec. 21, 2018.

(51) Int. Cl.
*A61M 25/02*    (2006.01)

(52) U.S. Cl.
CPC ....... *A61M 25/02* (2013.01); *A61M 2025/024* (2013.01); *A61M 2025/0213* (2013.01); *A61M 2025/0246* (2013.01); *A61M 2025/0253* (2013.01)

(58) Field of Classification Search
CPC .......... A61M 25/02; A61M 2025/0206; A61M 2025/0213; A61M 2025/024; A61M 2025/0246; A61M 2025/028
See application file for complete search history.

(56) References Cited

U.S. PATENT DOCUMENTS

| | | | |
|---|---|---|---|
| 3,444,861 A | 5/1969 | Schulte | |
| 4,050,461 A | 9/1977 | Ruby | |
| 4,149,539 A * | 4/1979 | Cianci | A61M 25/02 |
| | | | 606/192 |
| 4,170,995 A | 10/1979 | Levine et al. | |

(Continued)

FOREIGN PATENT DOCUMENTS

| | | |
|---|---|---|
| CN | 201988025 U | 9/2011 |
| EP | 0228826 A2 | 7/1987 |

(Continued)

OTHER PUBLICATIONS

International Search Report and Written Opinion dated Mar. 10, 2020 from correspondence PCT Application No. PCT/US2019/067859.

(Continued)

*Primary Examiner* — Nilay J Shah
(74) *Attorney, Agent, or Firm* — Honigman LLP

(57) ABSTRACT

An external catheter stabilizer device for stabilizing and retaining a catheter tube includes a base portion configured to adhesively attach at a patient, a retaining element configured to retain a catheter tube thereat, and a pivot element that pivotally attaches the retaining element to the base portion so as to allow for pivotal movement of the retaining element about a pivot axis generally normal to the patient where the base portion is attached. The retaining element includes a guide pin protruding therefrom and spaced from the pivot element. Pivotal movement of the retaining element relative to the base portion is limited to a selected range via engagement of the guide pin of the retaining element with an arcuate slot at the base portion.

18 Claims, 34 Drawing Sheets

(56) References Cited

U.S. PATENT DOCUMENTS

| | | | |
|---|---|---|---|
| 4,360,025 A | 11/1982 | Edwards | |
| 4,392,854 A | 7/1983 | Ibach | |
| 4,397,647 A | 8/1983 | Gordon | |
| 4,435,174 A | 3/1984 | Redmond et al. | |
| D287,166 S | 12/1986 | Lipsky et al. | |
| 4,645,492 A | 2/1987 | Weeks | |
| 4,660,555 A | 4/1987 | Payton | |
| 4,664,113 A * | 5/1987 | Frisbie | A61M 25/01 600/434 |
| 4,820,274 A | 4/1989 | Choksi et al. | |
| 5,052,411 A | 10/1991 | Schoolman | |
| 5,069,206 A | 12/1991 | Crosbie | |
| 5,196,019 A | 3/1993 | Davis et al. | |
| D337,383 S | 7/1993 | Smith | |
| D339,864 S | 9/1993 | Stern | |
| D342,134 S | 12/1993 | Mongeon | |
| 5,267,969 A | 12/1993 | Hirsch et al. | |
| 5,318,581 A | 6/1994 | Sunmo | |
| D349,765 S | 8/1994 | Russo | |
| 5,352,211 A | 10/1994 | Merskelly | |
| D363,778 S | 10/1995 | Cane et al. | |
| D364,457 S | 11/1995 | Mongeon | |
| 5,685,859 A | 11/1997 | Kornerup | |
| 5,690,616 A | 11/1997 | Mogg | |
| 5,693,032 A | 12/1997 | Bierman | |
| 5,916,200 A | 6/1999 | Eppley et al. | |
| 5,944,696 A | 8/1999 | Bayless et al. | |
| 6,074,368 A | 6/2000 | Wright | |
| 6,213,979 B1 | 4/2001 | Bierman | |
| 6,361,523 B1 | 3/2002 | Bierman | |
| 6,387,076 B1 | 5/2002 | Landuyt | |
| 6,413,240 B1 | 7/2002 | Bierman et al. | |
| 6,428,514 B1 | 8/2002 | Goebel et al. | |
| D462,443 S | 9/2002 | Webb | |
| 6,582,403 B1 | 6/2003 | Bierman et al. | |
| 6,663,600 B2 | 12/2003 | Bierman et al. | |
| 7,074,208 B2 * | 7/2006 | Pajunk | A61M 25/02 128/DIG. 6 |
| 7,204,827 B2 * | 4/2007 | Kessler | A61M 25/02 128/DIG. 26 |
| 7,223,256 B2 * | 5/2007 | Bierman | A61M 25/02 604/174 |
| 7,344,512 B2 | 3/2008 | Yamazaki et al. | |
| 7,563,251 B2 | 7/2009 | Bierman et al. | |
| 7,762,991 B2 | 7/2010 | Bierman et al. | |
| 7,837,655 B2 | 11/2010 | Bierman et al. | |
| 7,922,697 B2 | 4/2011 | Beran | |
| 7,935,084 B2 | 5/2011 | Bierman | |
| 7,947,021 B2 | 5/2011 | Bourne et al. | |
| 7,955,307 B2 | 6/2011 | Bierman et al. | |
| 7,985,205 B2 | 7/2011 | Adams | |
| 8,025,643 B2 | 9/2011 | Bierman | |
| 8,052,649 B2 | 11/2011 | Wright | |
| 8,177,756 B2 * | 5/2012 | Wright | A61M 25/02 604/174 |
| 8,298,191 B2 | 10/2012 | Bierman et al. | |
| 8,308,740 B2 | 11/2012 | Tolley et al. | |
| 8,394,065 B2 | 3/2013 | Bierman | |
| 8,398,599 B2 | 3/2013 | Bierman | |
| 8,540,680 B2 | 9/2013 | Burn | |
| 8,636,699 B2 | 1/2014 | Russo | |
| 8,684,976 B2 | 4/2014 | Bierman et al. | |
| 8,734,401 B2 | 5/2014 | Beran | |
| 8,740,876 B2 | 6/2014 | Aguirre et al. | |
| 8,771,231 B2 | 7/2014 | Makino et al. | |
| 8,900,195 B2 | 12/2014 | Delegge et al. | |
| 8,936,025 B2 | 1/2015 | Flagler et al. | |
| 9,056,186 B2 | 6/2015 | Wright et al. | |
| D757,935 S | 5/2016 | Solingen et al. | |
| 9,526,871 B2 | 12/2016 | Wright et al. | |
| 9,638,354 B1 | 5/2017 | Ogueli et al. | |
| 9,642,987 B2 | 5/2017 | Bierman et al. | |
| 9,642,988 B2 | 5/2017 | Mizoguchi et al. | |
| D811,604 S | 2/2018 | Hashimoto et al. | |
| D814,026 S | 3/2018 | Darras et al. | |
| 9,974,929 B2 | 5/2018 | Ciccone et al. | |
| 10,034,971 B2 | 7/2018 | Abu-Sultaneh et al. | |
| 10,086,168 B2 | 10/2018 | Olson et al. | |
| 10,092,729 B2 | 10/2018 | Beran | |
| 2001/0011164 A1 | 8/2001 | Bierman | |
| 2002/0103481 A1 | 8/2002 | Webb et al. | |
| 2005/0267373 A1 | 12/2005 | Lee | |
| 2007/0149878 A1 | 6/2007 | Hankins | |
| 2008/0249476 A1 | 10/2008 | Bierman et al. | |
| 2008/0300546 A1 | 12/2008 | Godara et al. | |
| 2009/0157000 A1 | 6/2009 | Waller | |
| 2011/0218498 A1 | 9/2011 | Bierman et al. | |
| 2011/0295210 A1 * | 12/2011 | Wright | A61M 25/02 604/180 |
| 2012/0046515 A1 | 2/2012 | Woo et al. | |
| 2012/0136314 A1 * | 5/2012 | Ciccone | A61M 25/0017 604/174 |
| 2014/0018778 A1 | 1/2014 | Lopera et al. | |
| 2014/0276543 A1 * | 9/2014 | Beran | A61M 25/02 604/500 |
| 2014/0364880 A1 | 12/2014 | Farnan et al. | |
| 2016/0074285 A1 | 3/2016 | Thomas | |
| 2016/0296725 A1 | 10/2016 | Calco | |
| 2019/0030289 A1 | 1/2019 | Olson et al. | |

FOREIGN PATENT DOCUMENTS

| | | | | |
|---|---|---|---|---|
| EP | 3085406 A1 * | 10/2016 | | A61M 25/02 |
| JP | 649656 | 1/1989 | | |
| KR | 101583712 B1 | 1/2016 | | |
| KR | 20160097532 A | 8/2016 | | |
| WO | 2000010637 A1 | 3/2000 | | |
| WO | 2001062328 A1 | 8/2001 | | |
| WO | 2006050080 A2 | 5/2006 | | |
| WO | 2015116571 A1 | 8/2015 | | |
| WO | 2016141291 A1 | 9/2016 | | |

OTHER PUBLICATIONS

Clik-Fix Picc/Contral Securement Device, Starboard Medical, Retrieved from: https://starboardmedical.com/clik-it-catheter-securement/, 2018.

Wilson, Mary, "Urinary catheter securement: what are the options?" NRC, Nov. 2015.

* cited by examiner

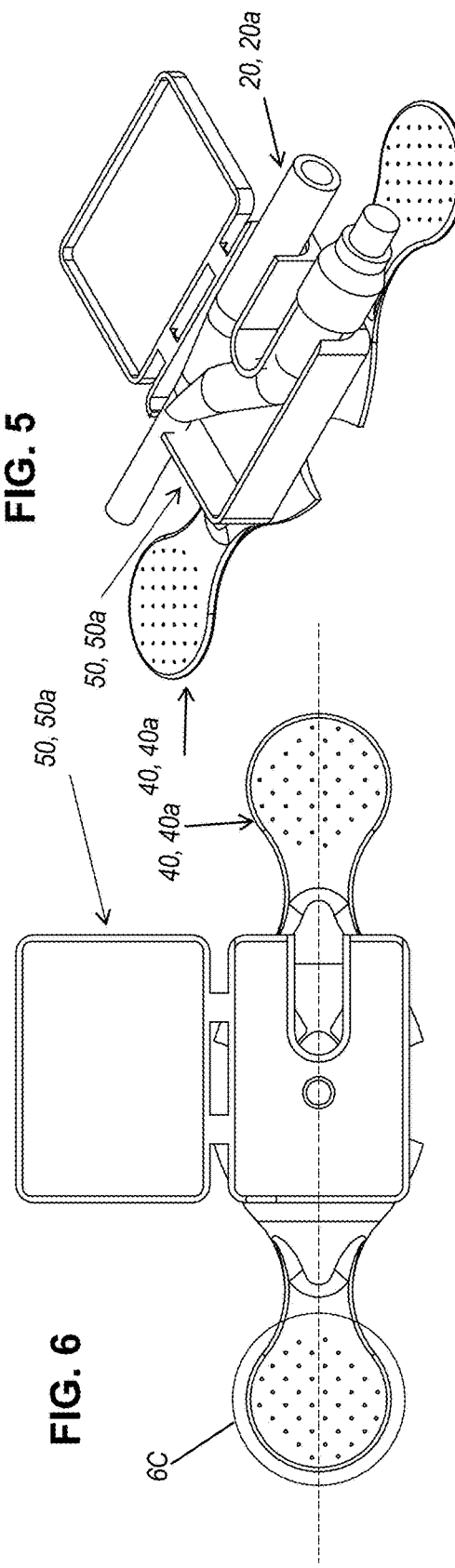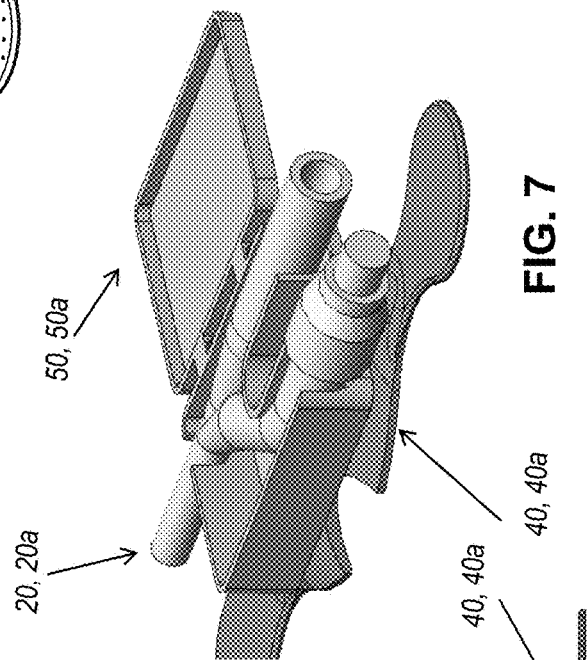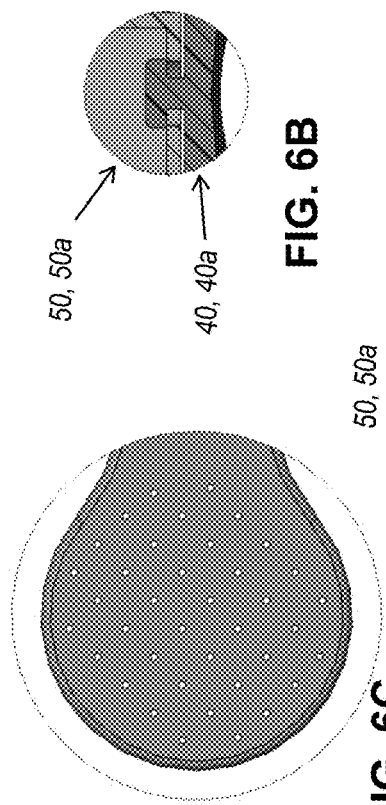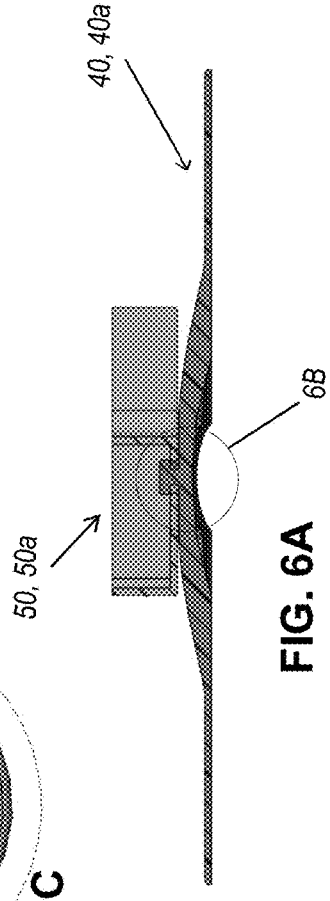

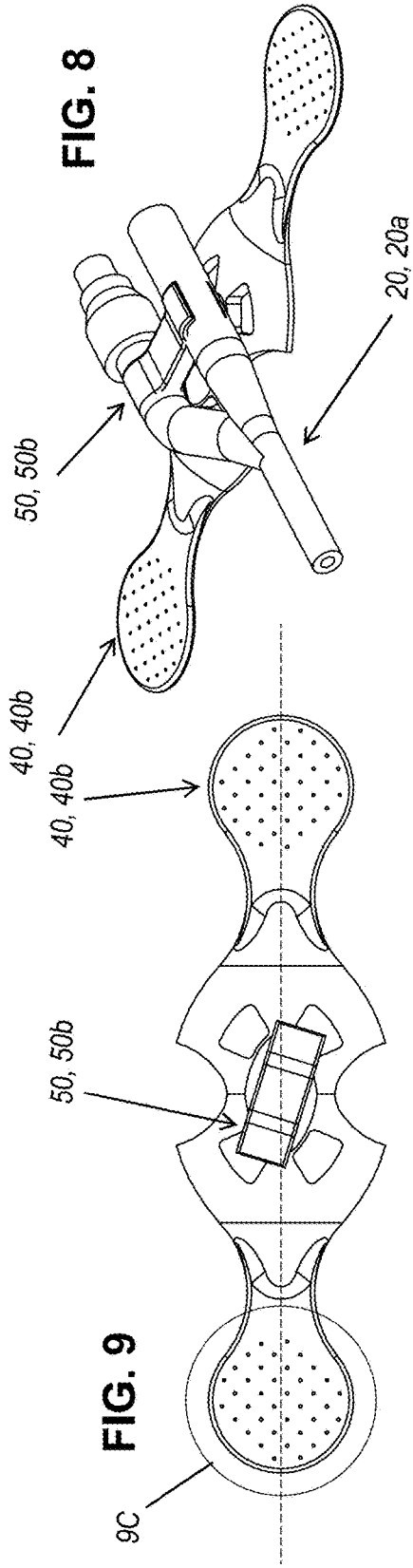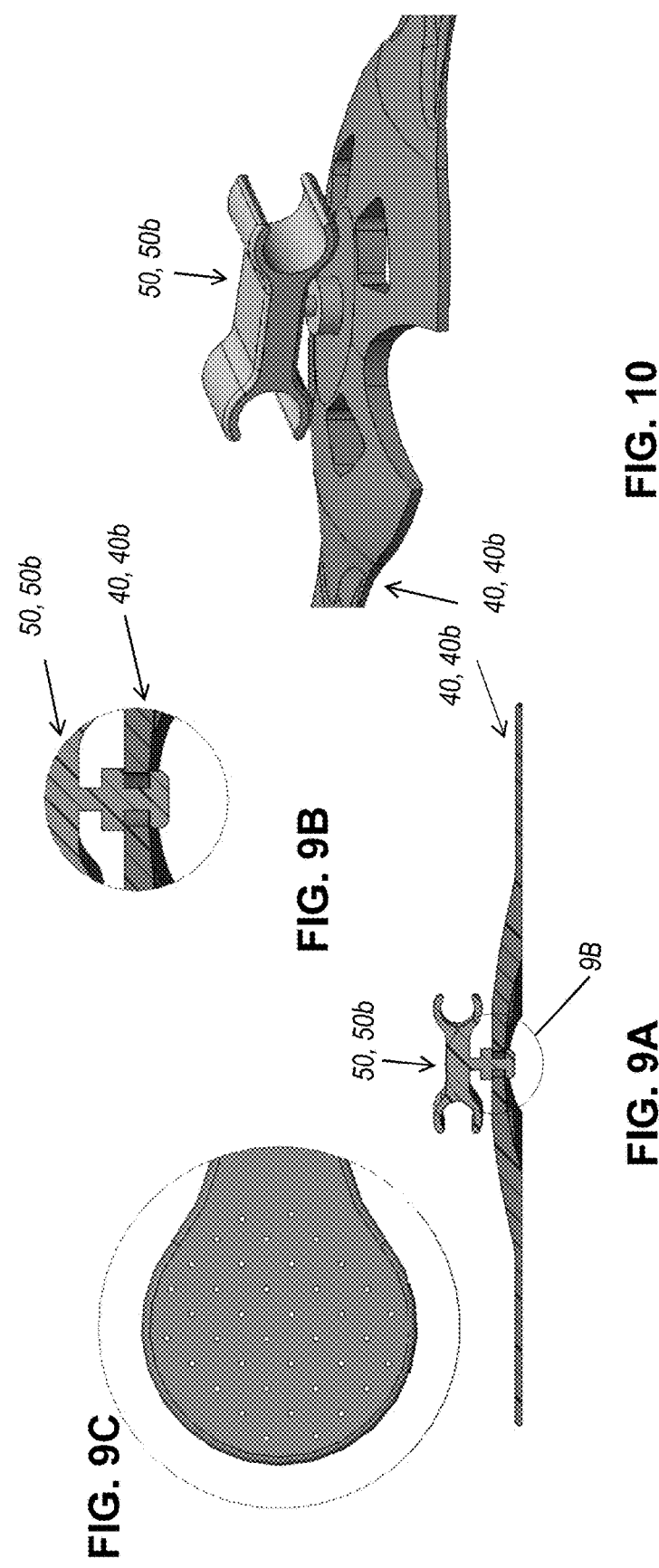

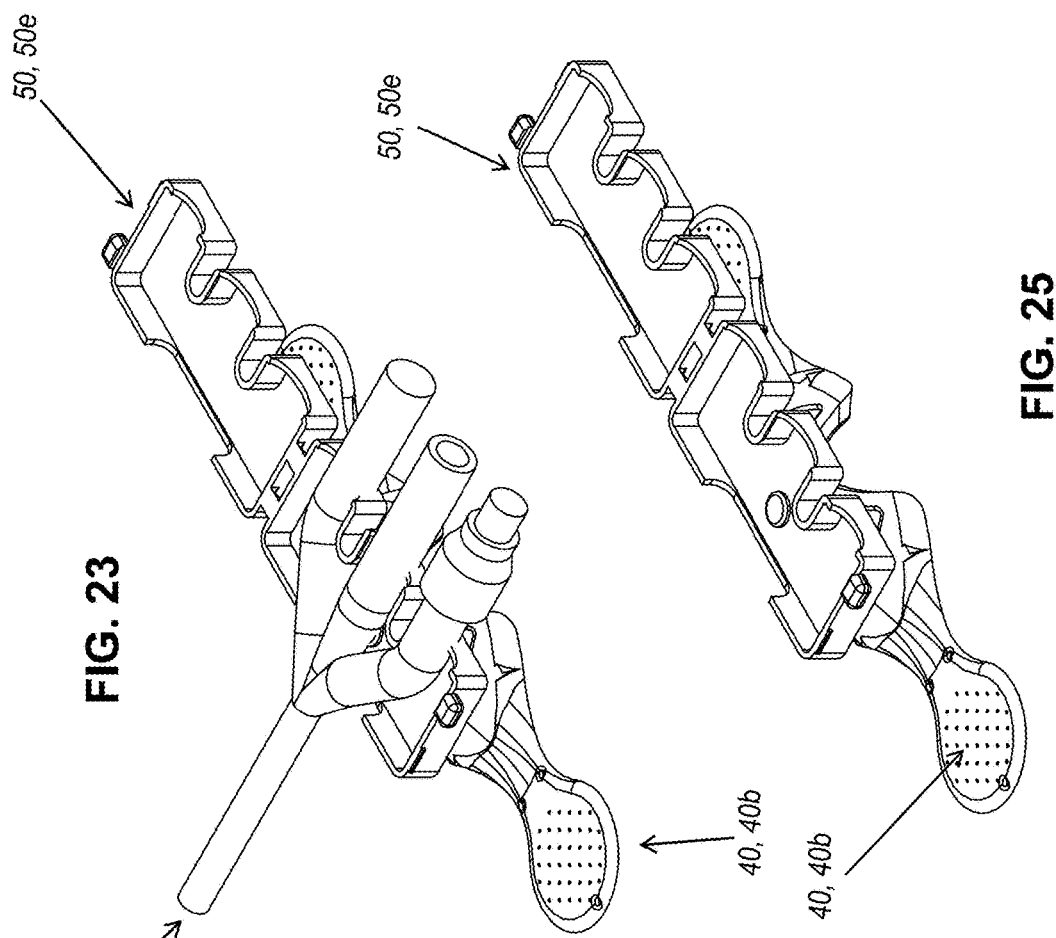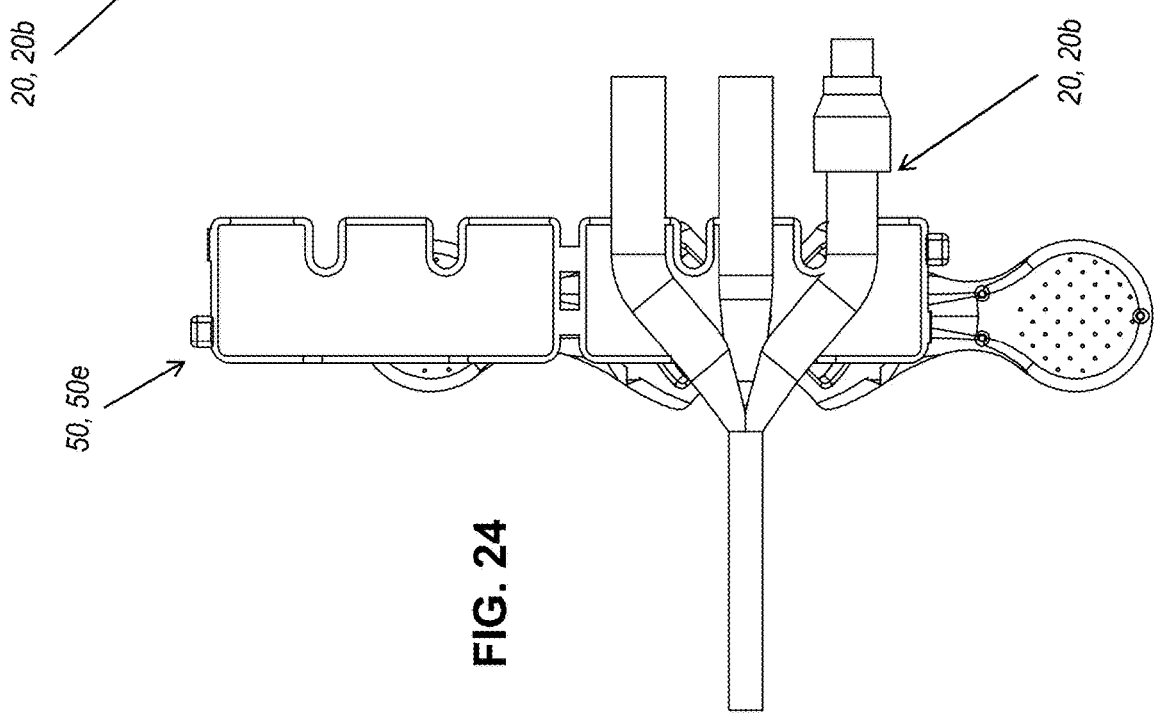

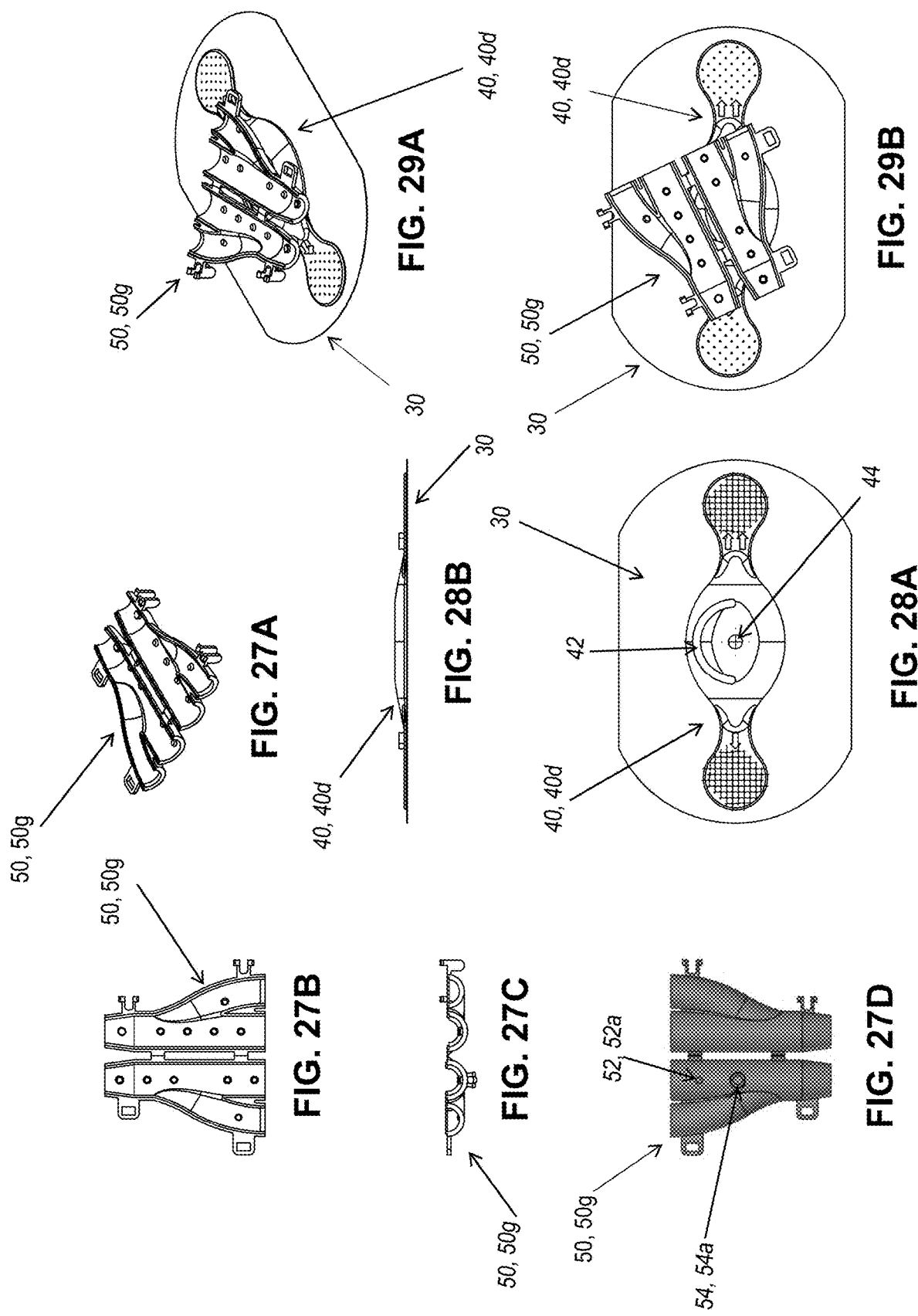

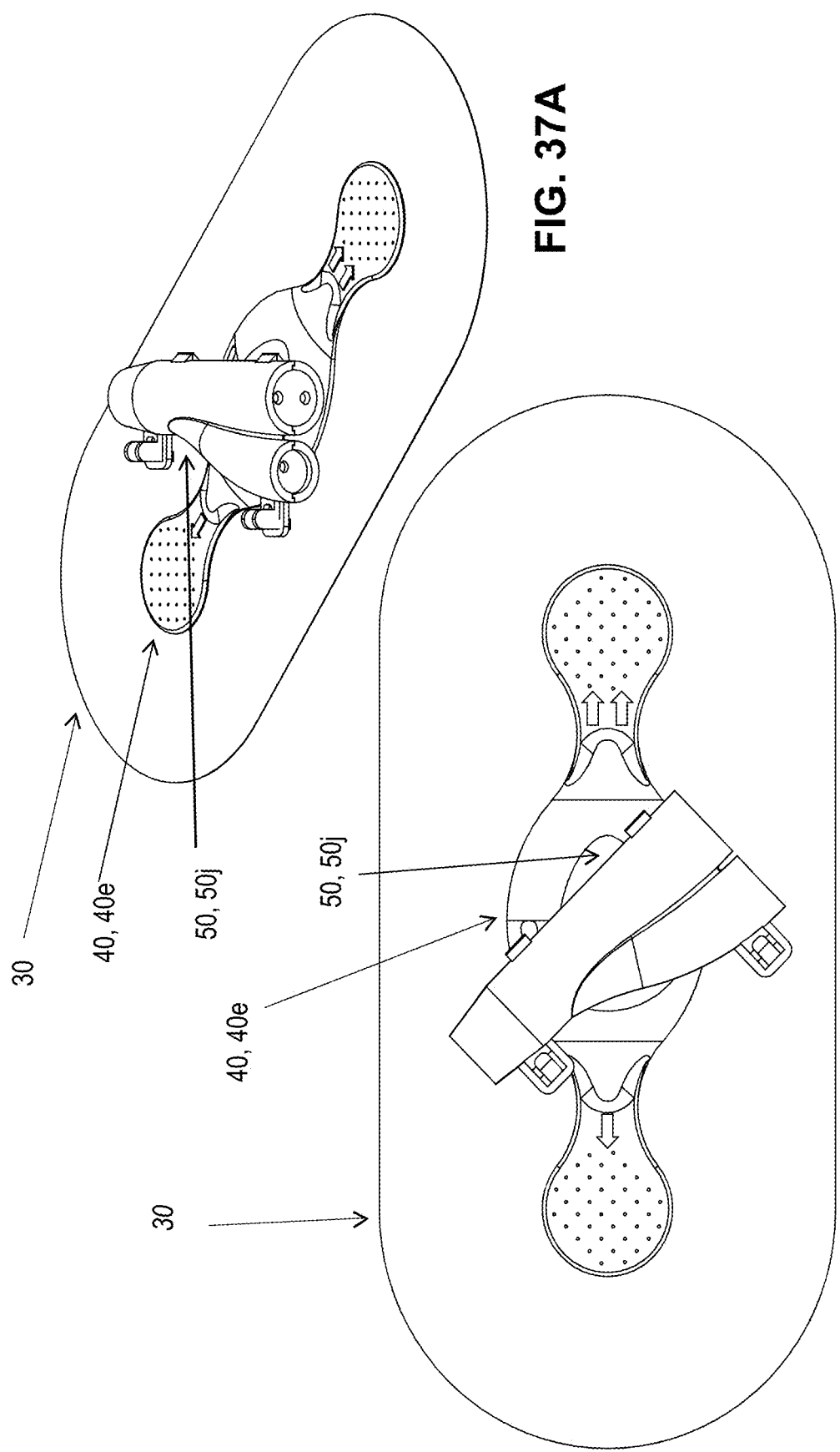

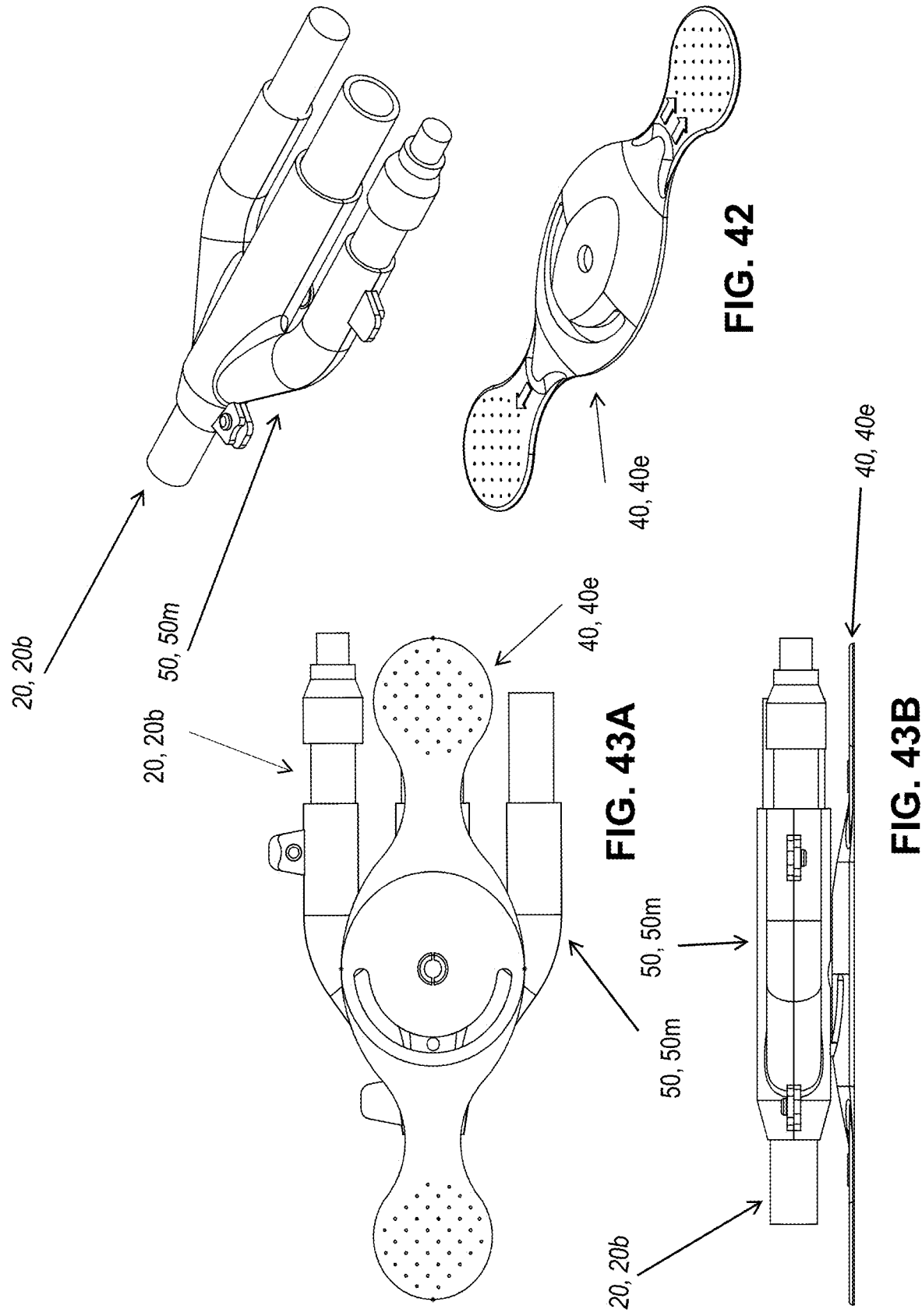

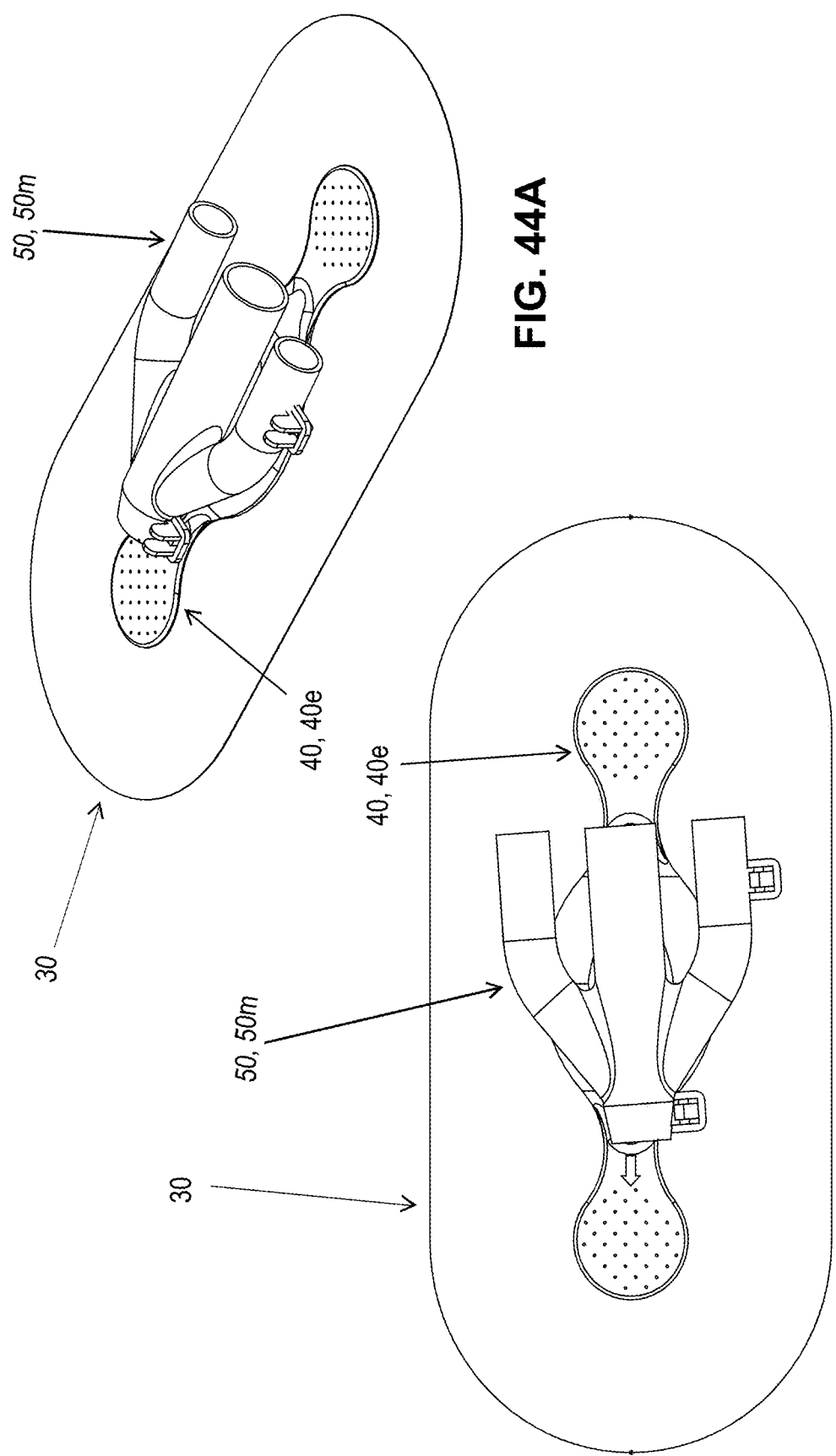

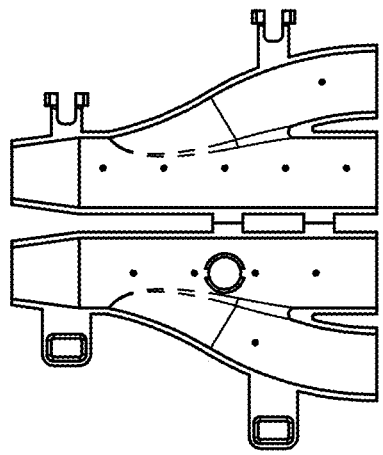
FIG. 56
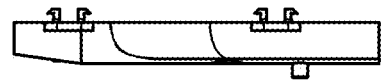
FIG. 59
FIG. 60
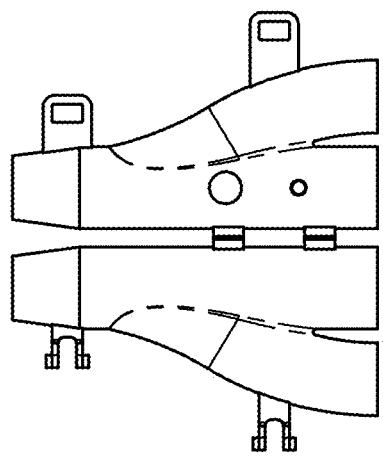
FIG. 58
FIG. 57

EXTERNAL CATHETER STABILIZER

CROSS REFERENCE TO RELATED APPLICATIONS

The present application claims the filing benefits of U.S. provisional applications, Ser. No. 62/826,057, filed Mar. 29, 2019, and Ser. No. 62/783,385, filed Dec. 21, 2018, which are hereby incorporated herein by reference in their entireties.

FIELD OF THE INVENTION

The present invention relates generally to control and stabilization of catheters and other similar generally flexible tubes comprised of medical-grade plastic or other known polymer materials, the purpose of which is for facilitating medical procedures related to draining or allowing for the drainage of bodily fluids or substantially liquid and flowable materials from the interior to the exterior portions of the human body for patients undergoing on-going, periodic, or one-time use medical treatments and procedures.

BACKGROUND OF THE INVENTION

When a patient/doctor is going to be using a catheter or a similar device to drain fluids from the body, dislodgment of the catheter at a surgically prepared stoma site can significantly increase the risk of infection and irritation to the surrounding skin and internal organs. Thus, various solutions have been proposed to retain a catheter in place at the patient. For example, for a bladder Mitrofanoff surgery, a Foley catheter leaves an inflated balloon-like device inside the bladder and can cause bladder spasms as it moves, hits, or comes in contact with the interior wall of the bladder. This can cause the patient to experience extreme pain and discomfort.

There are some types of other catheter stabilizers that are not placed over the stoma site which gives ample opportunity for the catheter to be accidentally or otherwise inadvertently pulled out of the bladder or stoma passageway. These types of devices tend to provide only a partial solution and fall short due to inherent limitations of their designs. Taping the catheter down directly to the surface of the skin is typically required, but this is not an adequate or long-term solution for patients needing to drain a bladder manually over an extended period of time, which is generally defined by the particular instance or length of the healing process of each particular patient. If the installed catheter is not closely monitored or otherwise carefully guarded, it may easily and inadvertently become mechanically pulled-on or get caught on something. In severe cases, it will rip out causing extreme pain, possible infection, irritation of the skin, and a possible revision or emergency repair surgery.

SUMMARY OF THE INVENTION

The present invention provides an external catheter stabilizer device that is positionable at the patient's skin (such as at the patient's leg) and allows for flexibility or pivoting of the tube at the attachment at the patient's skin to allow for movement of the patient without pulling at the catheter tube where it enters the patient's body.

In accordance with an aspect of the invention, the external catheter stabilizer device includes a base portion configured to adhesively attach at a patient, a retaining element configured to retain the catheter tube thereat, and a pivot element that pivotally attaches the retaining element to the base portion. The pivot element attaches to the retaining element so as to allow for pivotal movement of the retaining element about a pivot axis generally normal or perpendicular to the patient's skin where the base portion is attached. Pivotal movement of the retaining element relative to the base portion is limited to a selected range via engagement of a guide pin of the retaining element with an arcuate slot at the base portion. The arcuate slot may extend 180 degrees about the pivot axis, limiting pivotal movement of the retaining element relative to the base portion to about 180 degrees.

In accordance with another aspect of the present invention, the external catheter stabilizer device includes a pivot element that pivotally attaches the retaining element to the base portion so as to allow for pivotal movement of the retaining element about a pivot axis generally normal to the patient where the base portion is attached. The pivot element detachably attaches the retaining element to the base portion. The retaining element may include a housing that is openable and closable, with the housing configured to limit or prevent detaching the retaining element from the base portion while the housing is closed.

These and other objects, advantages, purposes and features of the present invention will become apparent upon review of the following specification in conjunction with the drawings.

BRIEF DESCRIPTION OF THE DRAWINGS

FIG. 5 is a perspective view of the device, shown with the retainer opened and a catheter tube disposed thereat;

FIG. 6 is a plan view of the device of FIG. 5, shown without the catheter tube;

FIG. 6A is a sectional view taken along the centerline of the device of FIG. 6;

FIG. 6B is an enlarged view of the pin and retainer connection of FIG. 6A;

FIG. 6C is an enlarged view of the pad of FIG. 6;

FIG. 7 is another perspective view of the device of FIG. 5;

FIG. 8 is a perspective view of another device, with the catheter tubes clipped to a pivotable retainer and base portion;

FIG. 9 is a plan view of the device of FIG. 8, shown without the catheter tubes;

FIG. 9A is a sectional view taken along the centerline of the device of FIG. 9;

FIG. 9B is an enlarged view of the pin and retainer connection of FIG. 9A;

FIG. 9C is an enlarged view of the pad of FIG. 9;

FIG. 10 is another perspective view of the device of FIG. 8, shown without the catheter tubes;

FIGS. 23-25 are perspective views of another retainer for retaining a three-tube catheter in accordance with the present invention;

FIGS. 27A-D are perspective and plan views of a retainer, shown in its open state, of another device in accordance with the present invention;

FIGS. 28A and 28B are plan and side views of a base and a skin adhesive patch of the device;

FIG. 29A is a perspective view of the assembled device including the components of FIGS. 27A-28B;

FIG. 29B is a plan view of the assembled device including the components of FIGS. 27A-28B;

FIG. 37A is a perspective view of the device of FIG. 35 including a skin adhesive patch;

FIG. 37B is a plan view of the device and patch of FIG. 37A;

FIG. 42 is an exploded perspective view of another device in accordance with the present invention;

FIGS. 43A and 43B are underside plan and side views of the device of FIG. 42;

FIG. 44A is a perspective view of the device of FIG. 42 including a skin adhesive patch;

FIG. 44B is a plan view of the device of FIG. 42 including the skin adhesive patch;

FIGS. 56 and 57 are plan views of the retainer of FIGS. 54 and 55;

FIGS. 58-60 are side and end elevations of the retainer of FIGS. 54 and 55;

DESCRIPTION OF THE PREFERRED EMBODIMENTS

Figure 1:
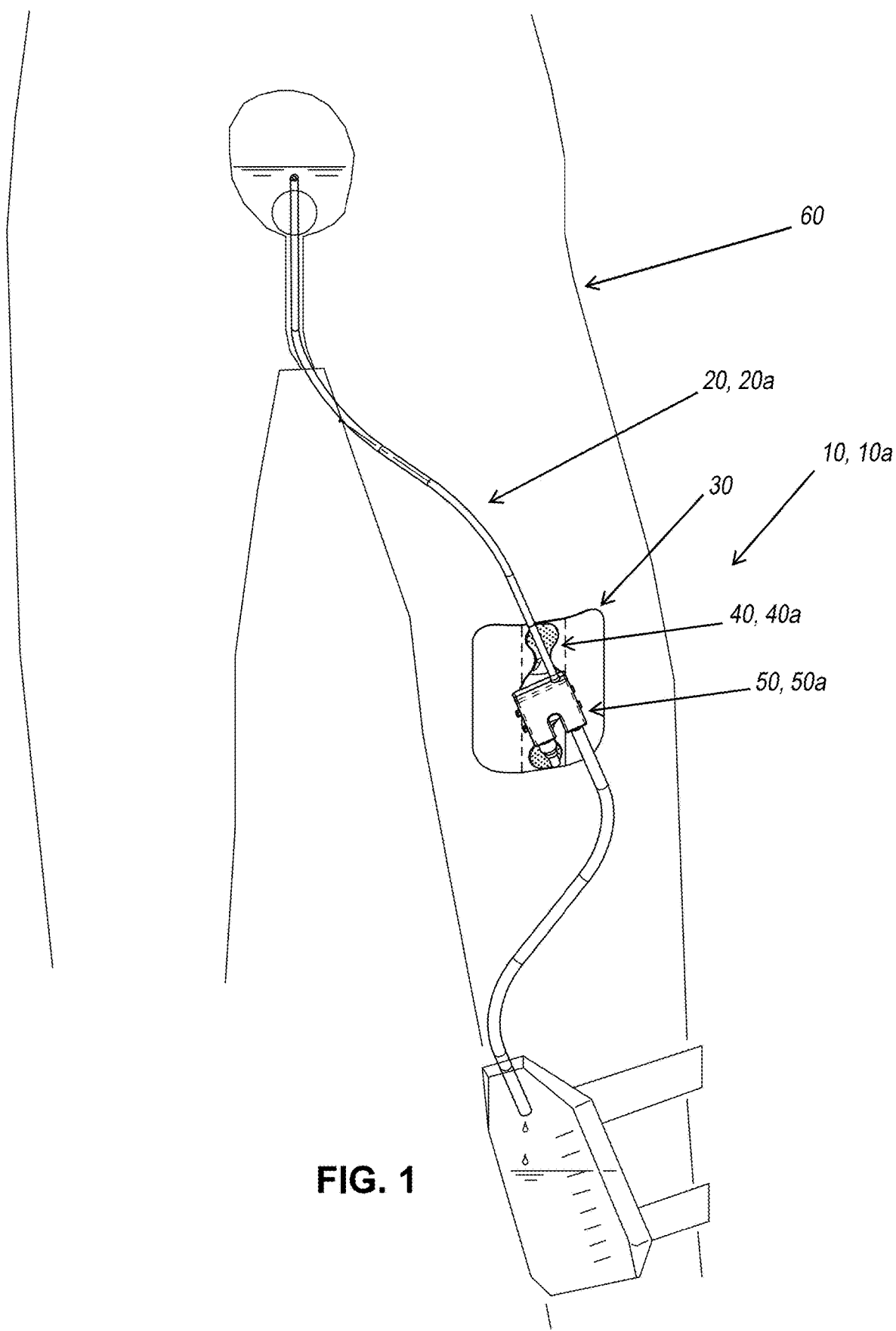
FIG. 1 is a perspective view of a urethral catheter holding device of the present invention, showing a complete arrangement including a currently Foley-style "balloon catheter" within the bladder of a patient, and with a commercially-available urine bag attached and supported by the leg of the patient by straps around the leg.
Figure 2:
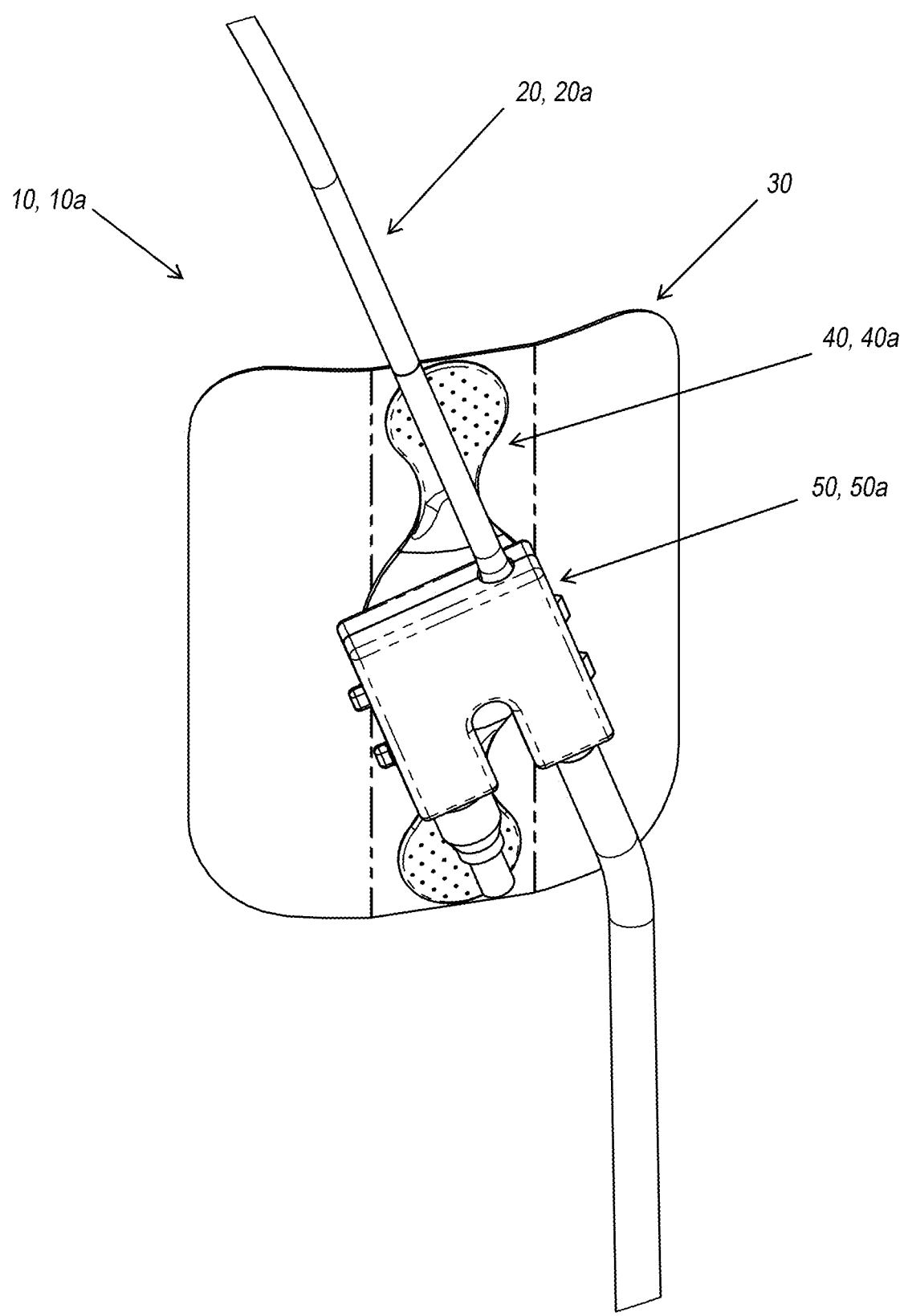
FIG. 2 is a close-up perspective view of the device of FIG. 1.
Figure 3:
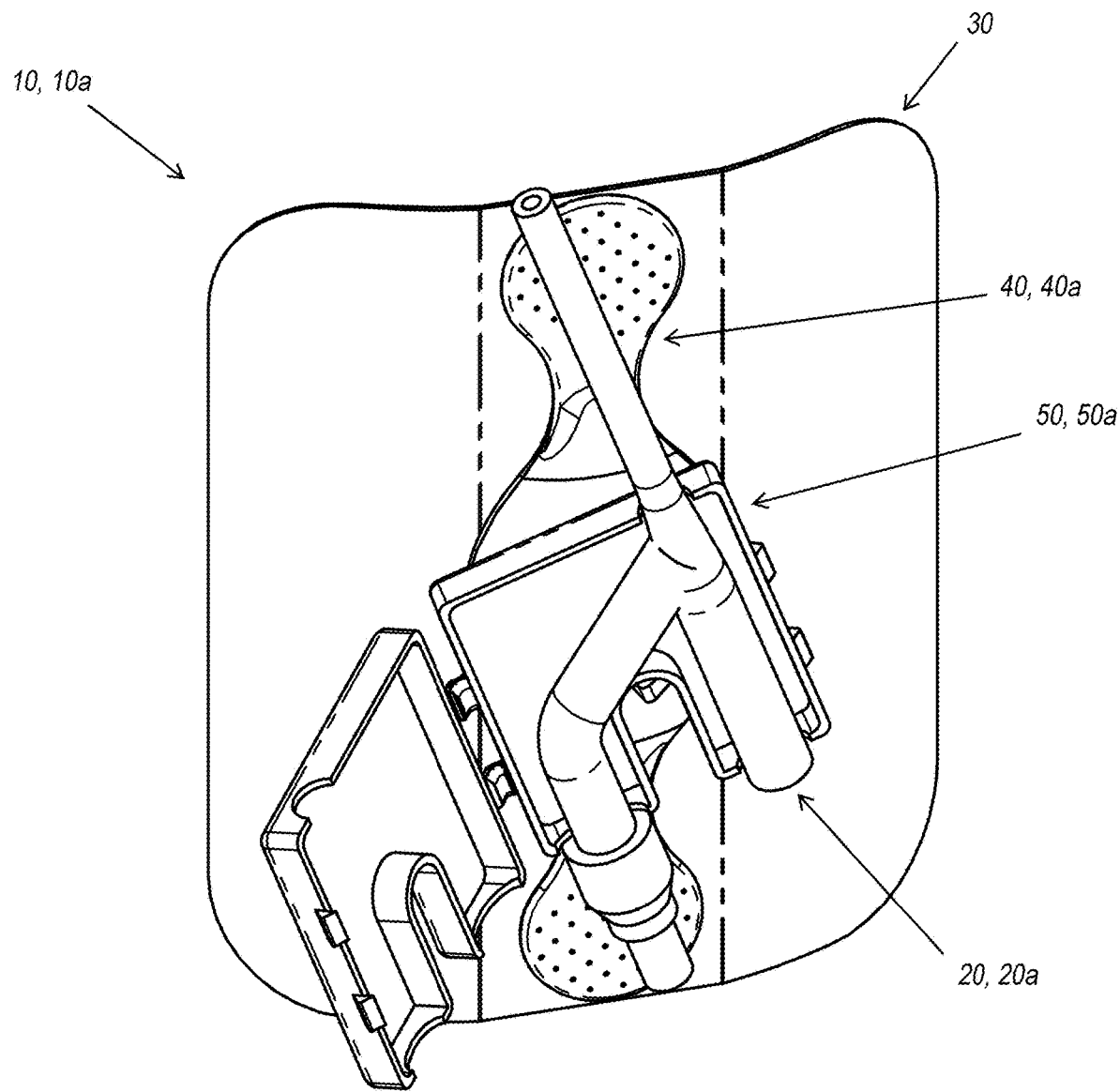
FIG. 3 is a close-up perspective view of the device of FIG. 2, showing the catheter stabilizer containment retainer in the "open" position.

Referring now to the drawings and the illustrative embodiments depicted therein, an external catheter stabilizer (ECS) device 10 provides support and retention of a catheter tube 20 at a patient 60.

Figure 4:
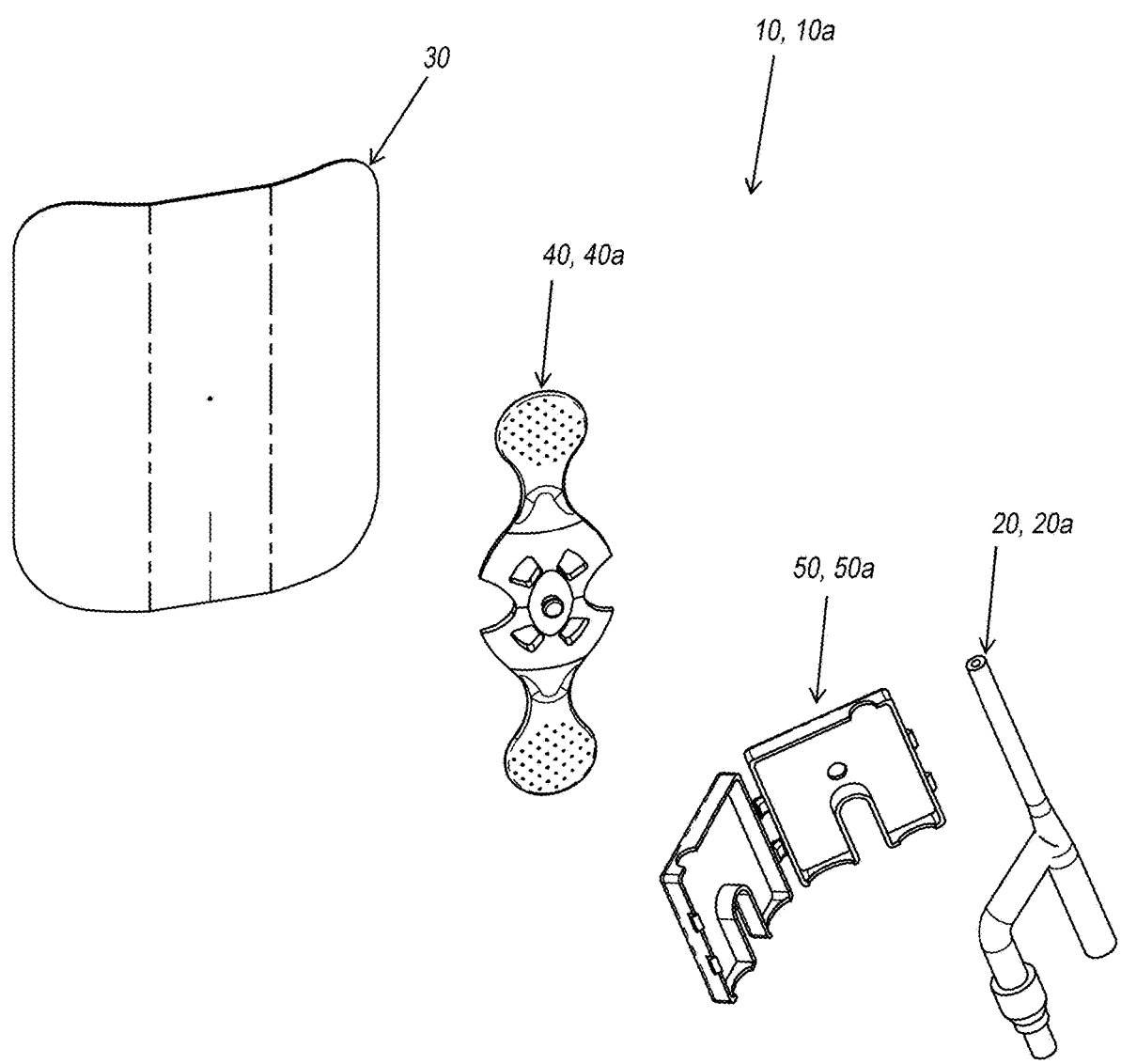
FIG. 4 shows an exploded view of the components shown in FIG. 3.
Figure 11:
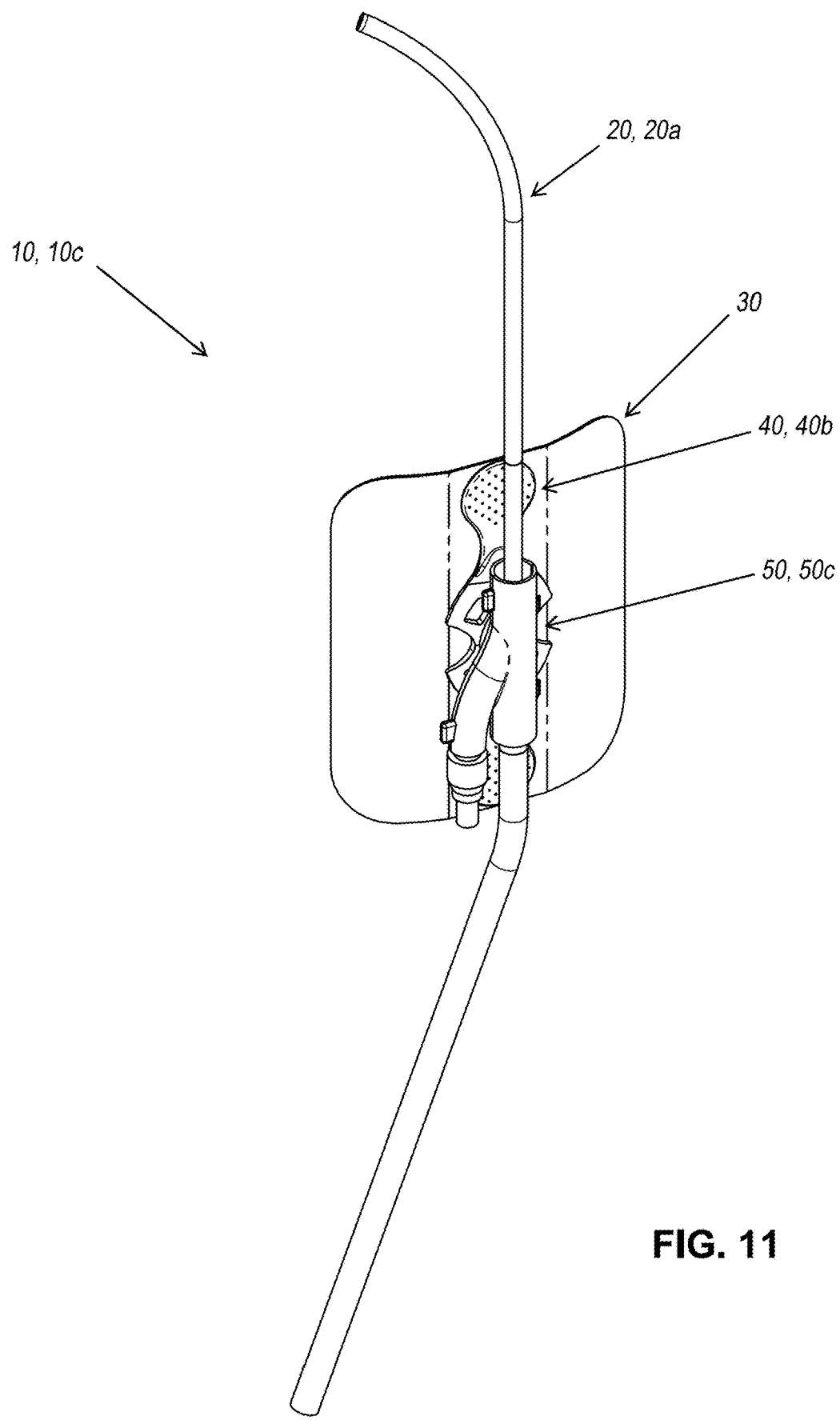
FIG. 11 is a perspective view of another device for retaining a two-tube catheter in accordance with the present invention, with the retainer comprising a generally Y-shaped element formed to receive the Y-junction of the catheter tube therein.
Figure 12:
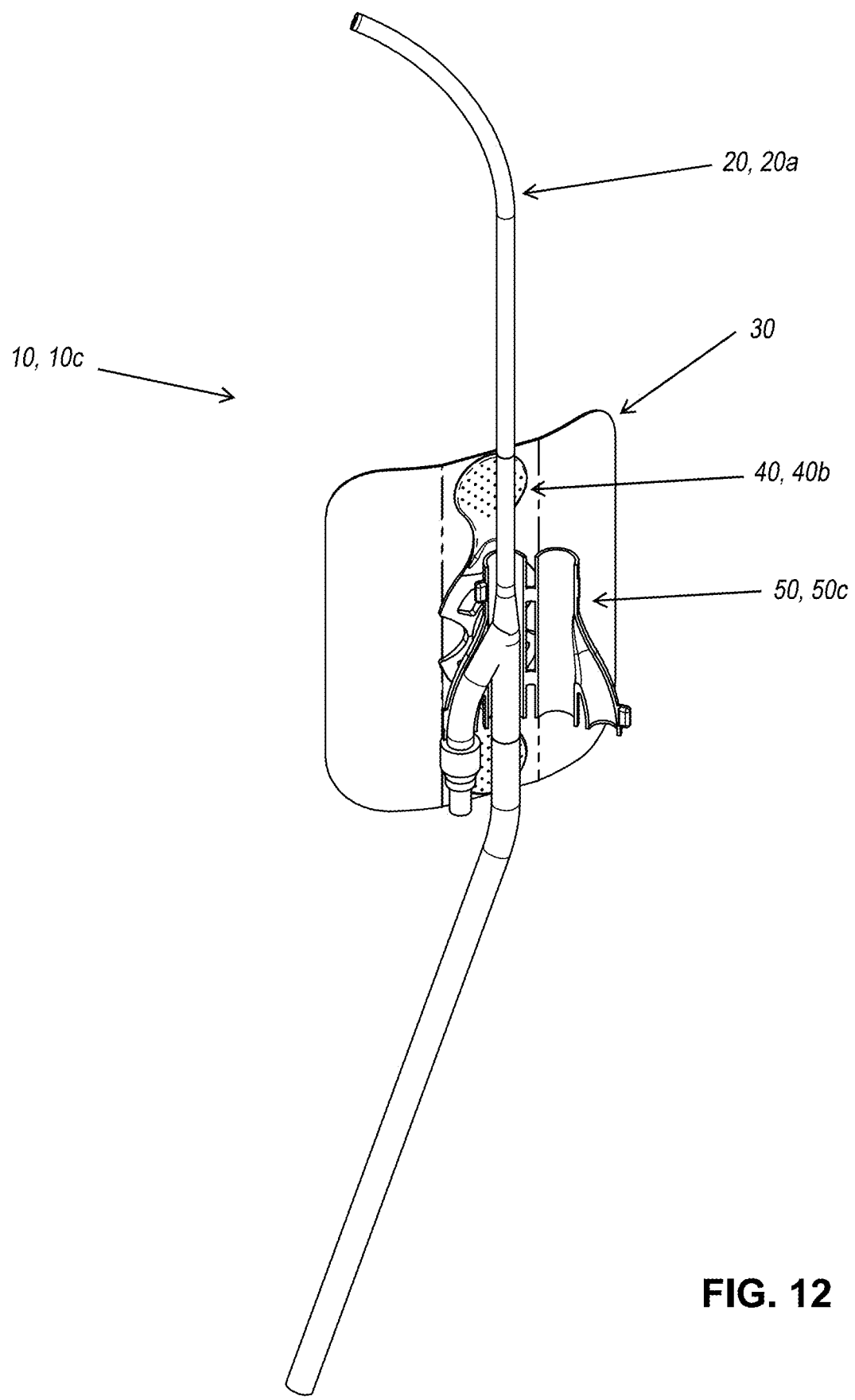
FIG. 12 is a perspective view of the device of FIG. 11, shown with the retainer in its opened state.
Figure 13:
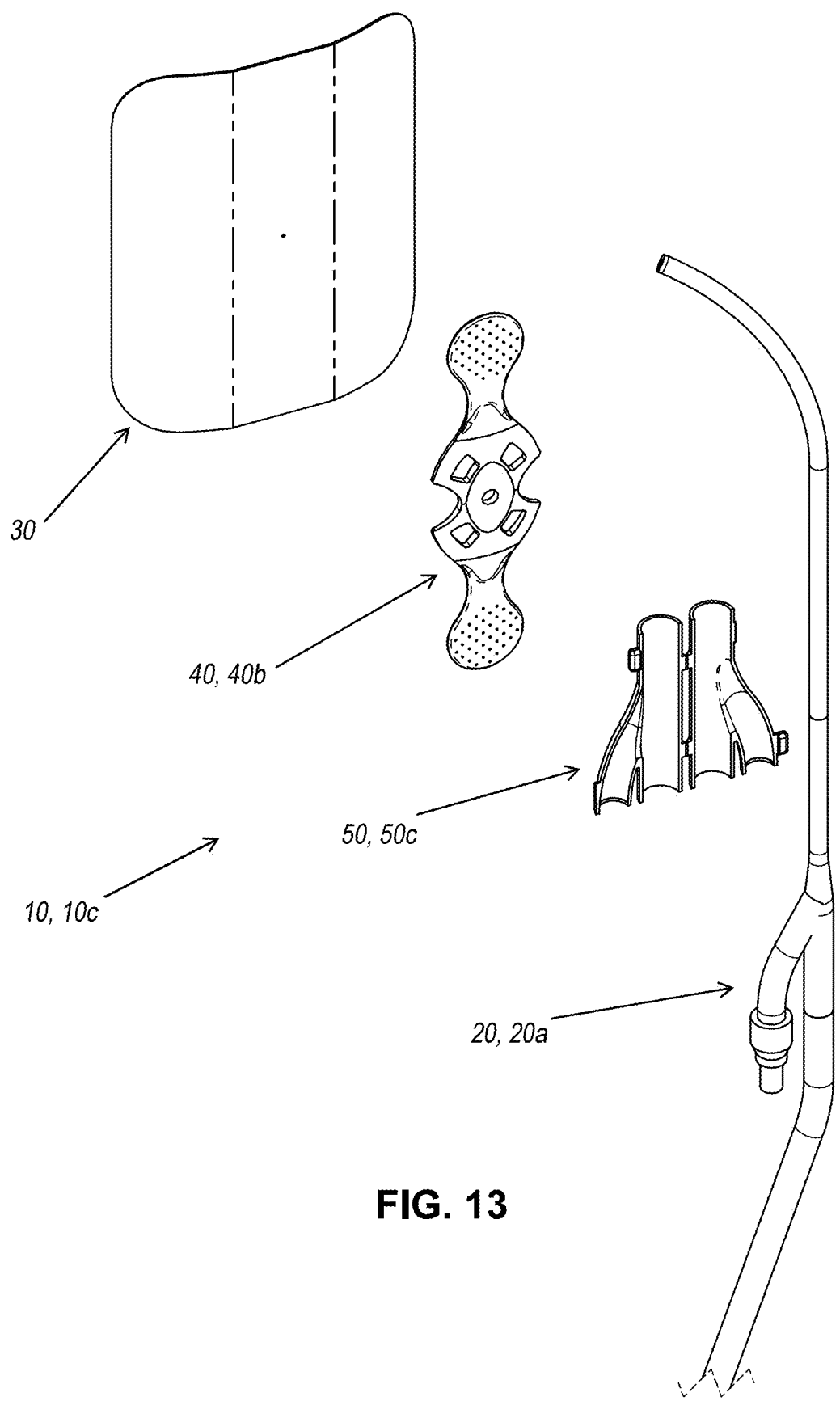
FIGS. 13 and 14 are exploded perspective views of the device of FIGS. 11 and 12.
Figure 14:
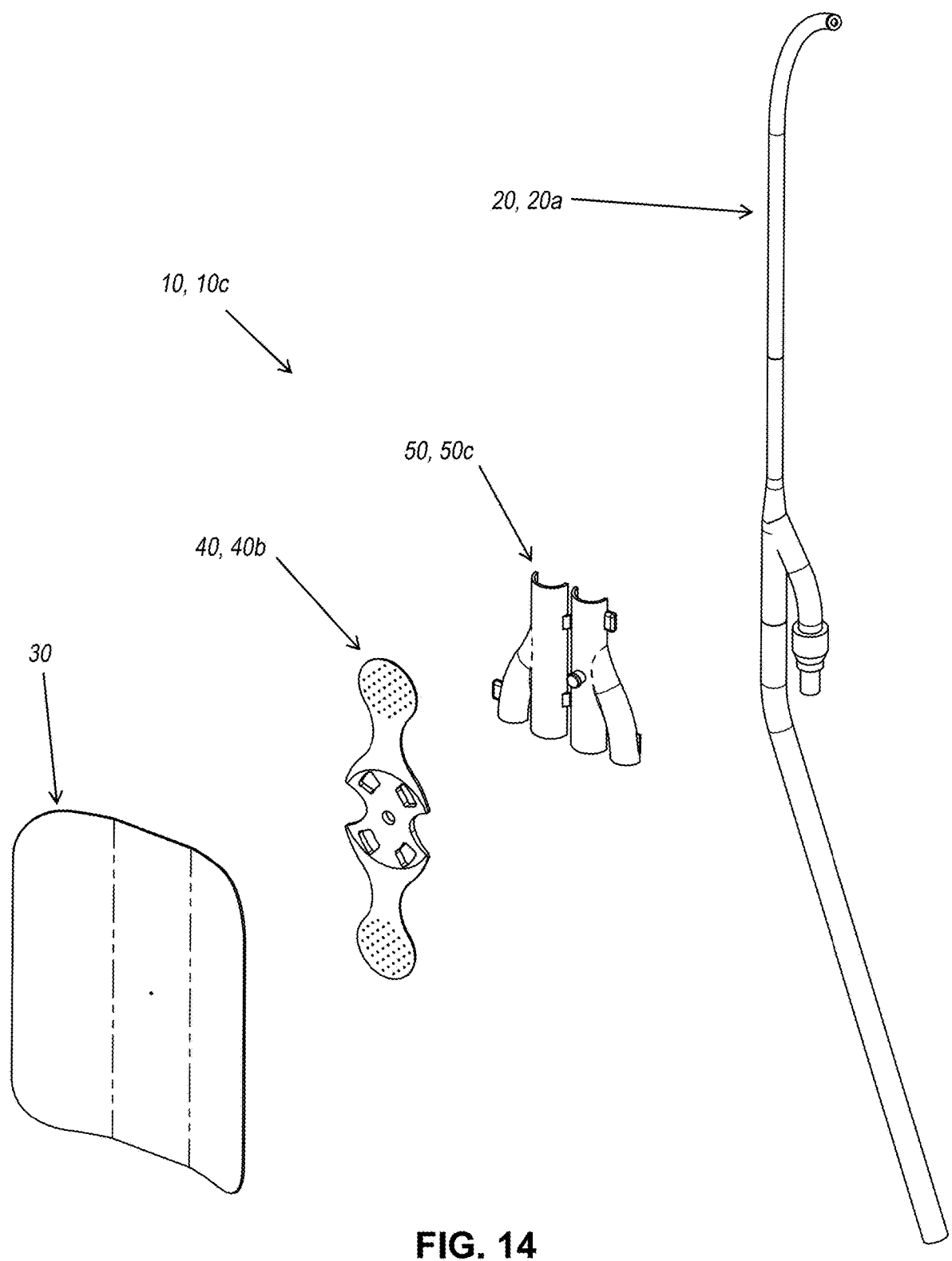
Figure 15:
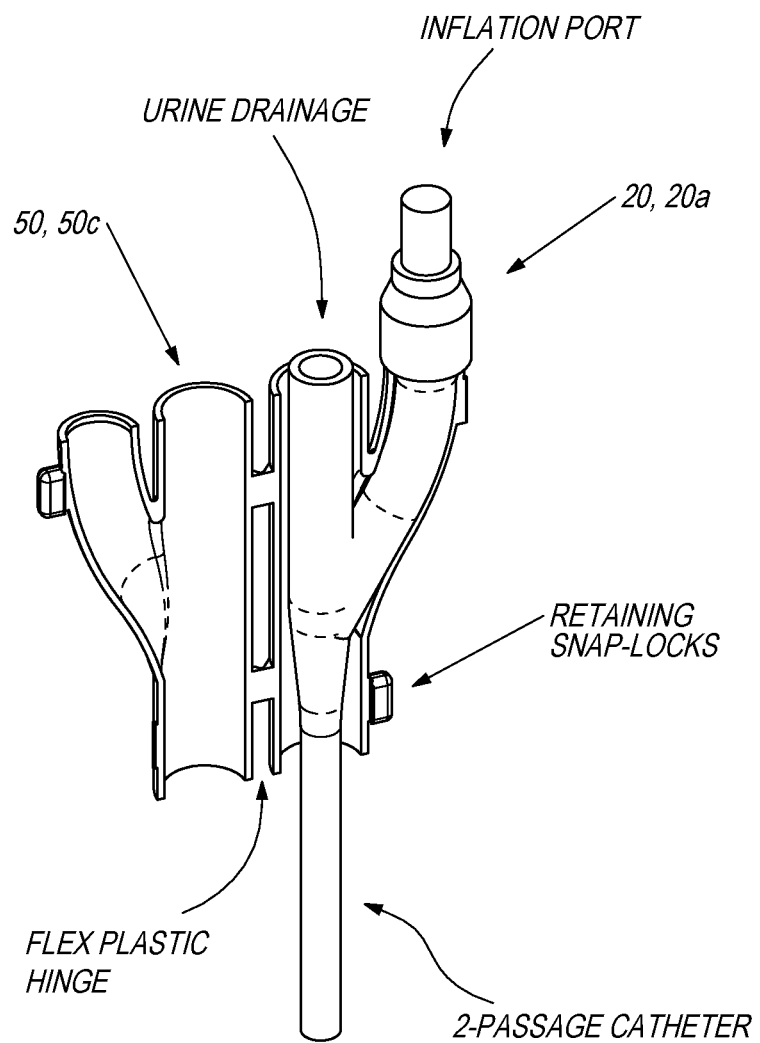
FIG. 15 is a close-up perspective view of the retainer, shown in its opened state.
Figure 16:
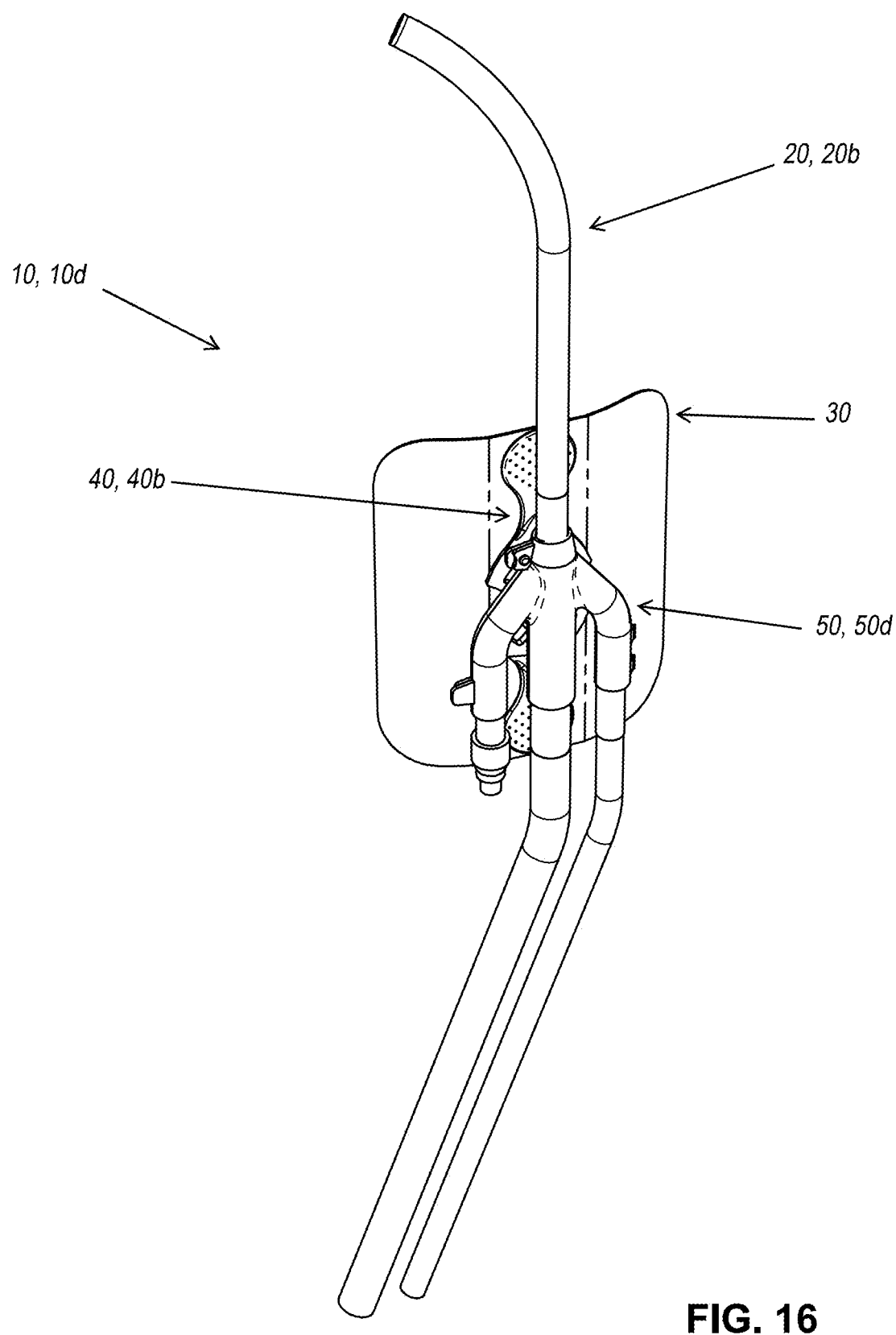
FIG. 16 is a perspective view of another device for retaining a three-tube catheter in accordance with the present invention, with the retainer comprising a shaped element formed to receive the three-way junction of the catheter tube therein.
Figure 17:
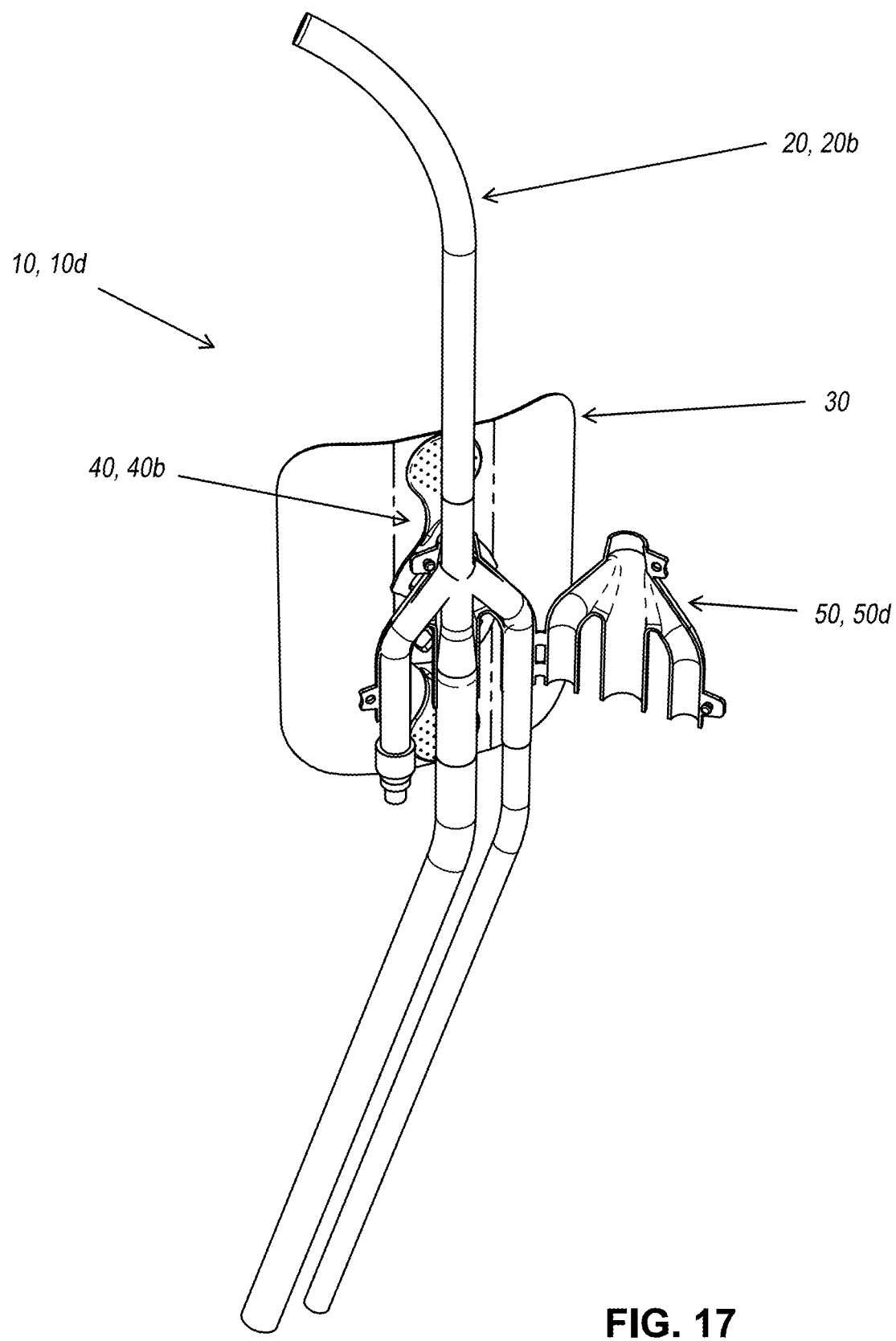
FIG. 17 is a perspective view of the device of FIG. 16, shown with the retainer in its opened state.
Figure 18:
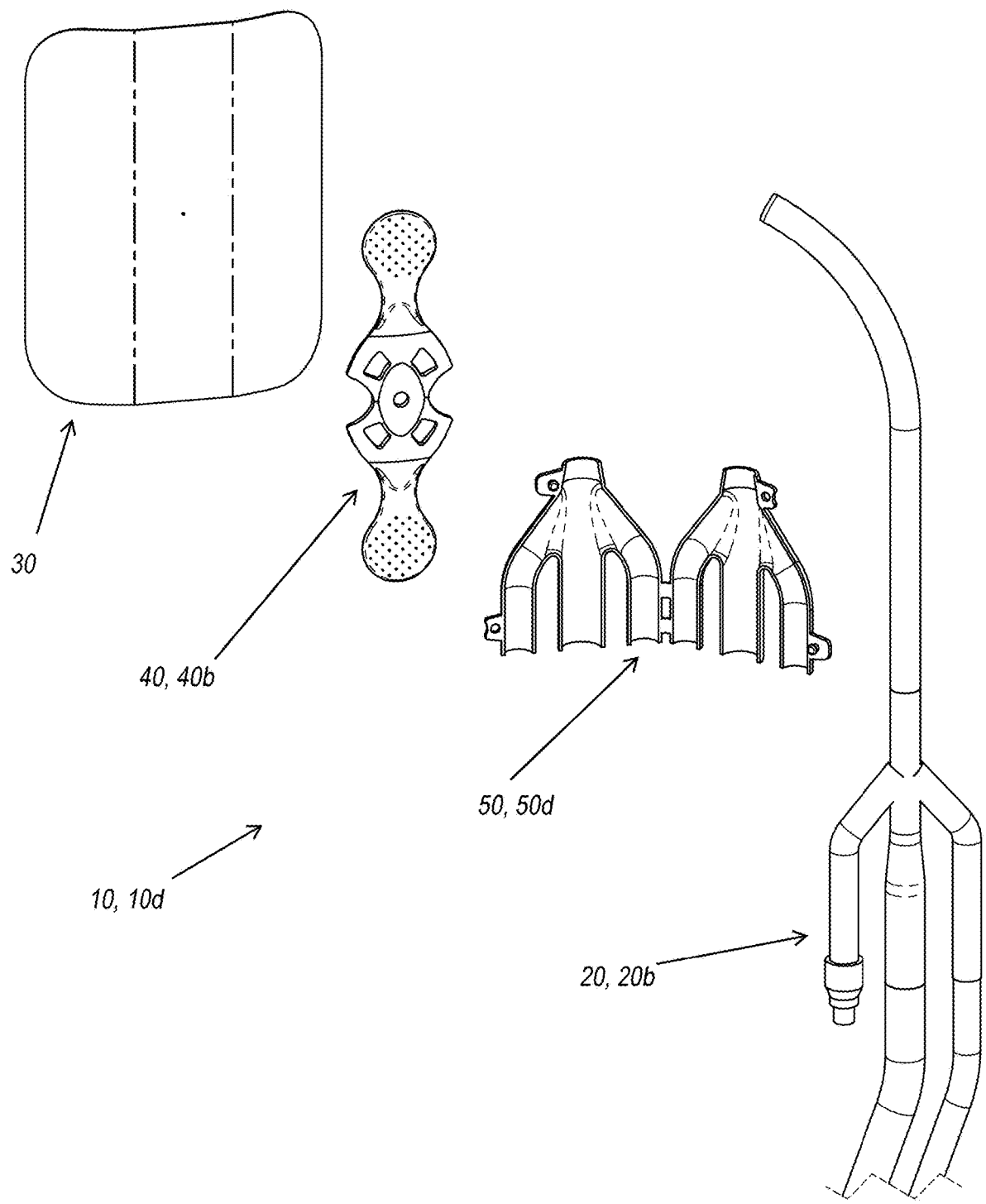
FIGS. 18 and 19 are exploded perspective views of the device of FIGS. 16 and 17.
Figure 19:
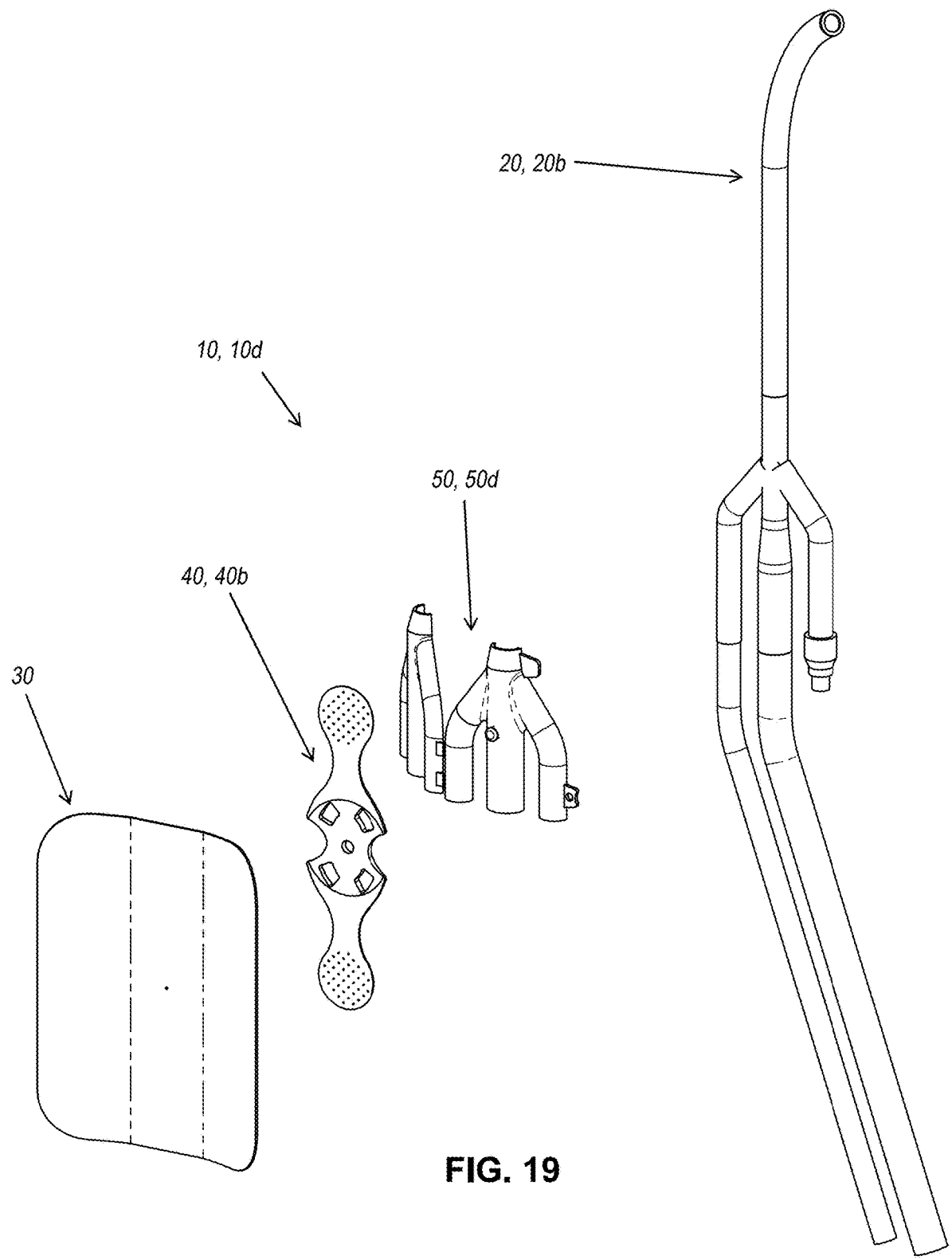
Figure 20:
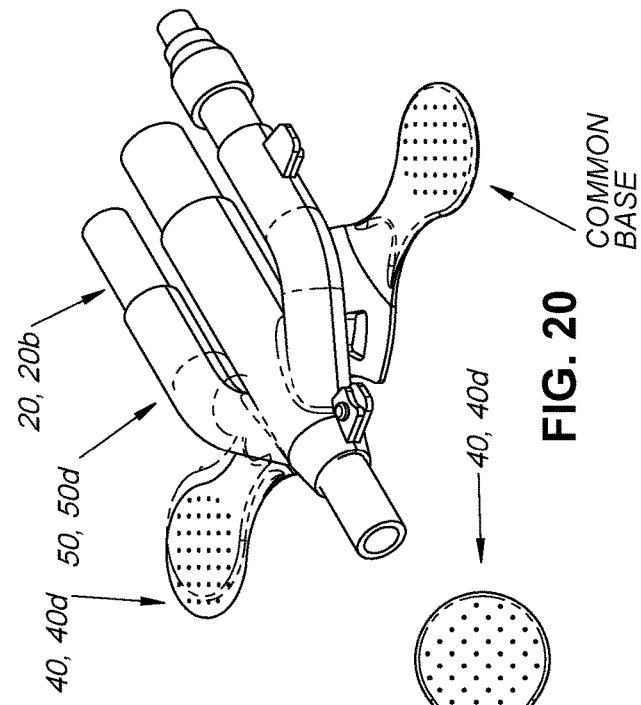
FIGS. 20-22 are close-up perspective views of the retainer of FIGS. 16 and 17.
Figure 21:
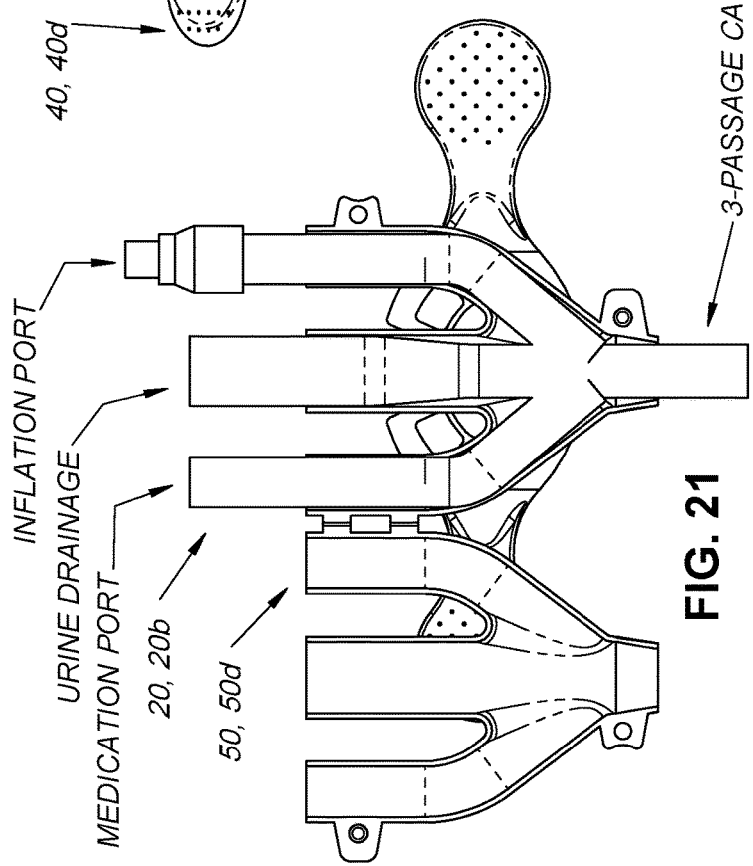
Figure 22:
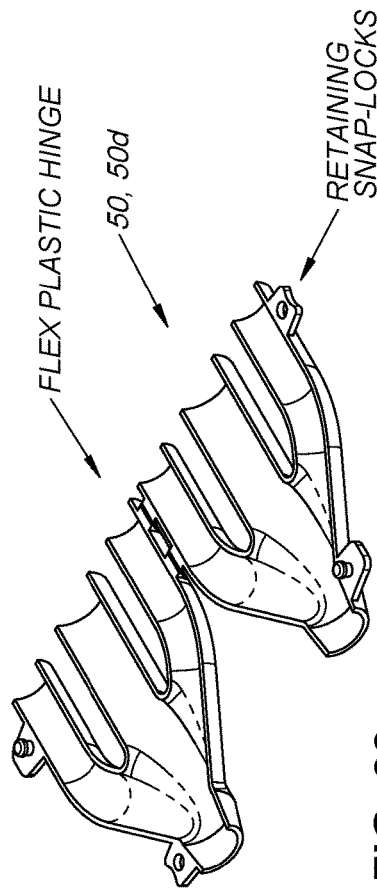

FIGS. 1-7 show a catheter holding device 10, 10a that includes a skin adhesive patch 30 (roughly for example, about 4 inches by about 4 inches (102 mm by 102 mm) in some implementations), a semi-flexible low-profile base 40, 40a attached to the skin adhesive patch 30, and a catheter stabilizer containment retainer 50, 50a (shown closed in FIG. 2 and opened in FIG. 3), which captures and encloses a typical Foley-style catheter "Y-junction." The retainer 50 may be made of, for example, somewhat rigid plastic as one piece incorporating molded-into place "living" plastic hinges to allow for opening and closing the retainer 50 and at least one molded-in plastic latch mechanism to secure the retainer 50 in the closed position. As shown in FIG. 4, a through-hole, generally centered in a wall at the base portion of the retainer 50a, engages with a "nail-head shaped protrusion" or pin at or near the center of the low-profile base 40a, with the hole in the retainer 50a and the pin at the base 40a simply snapped together to provide rotational engagement of the retainer 50a with respect to the base 40a. Thus, the adhesive patch 30 (skin compatible adhesive) is adhered to the skin of the patient 60, and the base 40a (comprising a semi-flexible urethane or the like) is adhesively attached (via an adhesive that may or may not be skin compatible) to the skin adhesive patch 30. The base 40a includes a pivot pin or element or structure that snaps through a pivot hole in the retainer 50a, whereby the two catheter tubes 20, 20a are positioned at the retainer 50a and retained thereat when the retainer 50a is closed. Optionally, the retainer may include a pivot element (e.g., pin or similar structure) protruding from a wall of the base portion of the retainer. The pivot element may snap through and rotationally engage with a compatible pivot hole in the base.

The device 10a provides a single axis of rotation of the retainer 50a relative to the patient's leg while also supporting the catheter 20a as needed for body movement of the patient 60. This arrangement helps to support and stabilize the catheter 20a and avoid placing unnecessary stress, strain, or disturbance to the patient's urethra tube and the Foley-style balloon inside the bladder of the patient 60.

Optionally, the retainer 50 may include a series of small flexible protrusions at one or more of the inward faces of the generally elliptical openings or passages in the retainer 50 where the catheter tube 20 passes through. The small flexible protrusions may be provided to create an increased or desired amount of friction between the catheter tube 20 and the closed retainer 50. This would help the retainer 50 better accommodate a wider range of catheter diameters, such as between, for example, 10 and 22 French catheter size diameters, inclusive.

With reference to FIGS. 8-10, a device 10, 10b of the present invention may have a retainer 50, 50b in the shape of a two-way clip that comprises a pin that pivotally attaches the clip to the base 40, 40b, whereby the tubes 20a simply snap into the two receiving clips of the device 10b. The two-way clip includes C-shaped clips at each end, with each C-shaped clip having a generally cylindrically shaped receiving portion or passageway with a predetermined inside diameter. The inside diameter dimensions at each C-shaped clip are selected by design, such that the clips frictionally engage the outer diameters of the catheter tubing of a given size (for example 10 through 22 French) to provide the desired degree of frictional engagement and securement of the catheter within the end portions of the pivotal clip. A selection of clips designed and pre-configured for an anticipated range of various standard diameter catheters, can optionally be made available to users. The various sizes of manufactured clips can be optionally identified by, for example, an imprinted number corresponding to the catheter size, different colors of injection molded plastic construction, or by other similar and appropriate means of rapid and helpful identification to the user. The user then simply selects the appropriate sized clip for a particular application and snaps the clip onto the base.

The overall product strategy and advantage with such embodiments is to secure and control a catheter 20a inserted directly into the urethra of a patient 60. The device 10b may be, for example, properly, reliably and consistently secured on or at a skin surface of the patient 60, such as via one or more adhesive pads using a particular adhesive selected for use with a person's skin. This provides an improvement over, for example, random use of simple and often generic medical tape, or simple and generic general-purpose adhesive patches. A problem exists when these materials are applied at random locations on the patient in random quantities and/or amounts by medical staff (or optionally, by the patient themselves) onto the patient's skin. This is often known to occur and is often a recurring problem and health risk in an effort to try to properly (and yet inconsistently) securely support the catheter tube to and with the patient. Use of various kinds of generic medical tape or adhesive patches can often tend to lead to inconsistent or inadequate securement of the catheter onto any given patient. Such patient-attempted tapes and adhesives are made to try to identify a solution to inadequate securement, which can be especially troublesome if the patient or catheter user tends to move around while in bed, while sleeping, awake, standing, walking, or if the patient or user is otherwise actively mobile to some degree in any way.

Use of medical tape by wrapping lengths of tape completely around a leg, arm or even the abdomen portion of the body in an effort to secure a catheter to the patient can result in discomfort and pain. This can be especially true with adverse reactions of the skin to various types of random glues or adhesives that may not be ideal for such purposes. In other more extreme cases, the improper use of lengths of tape that are simply banded completely around a portion of the body can possibly restrict the free flow of bodily fluids and/or the blood supply through the body. Such a condition may result in further serious medical complications, especially with respect to young children and elderly patients that may have to utilize catheters for various heath related reasons.

Another overall product strategy and advantage with the device of the present invention is to secure and control a catheter inserted directly over a surgically enabled opening in the body, or for example, a stoma opening leading to the bladder through the abdomen. Another overall product strategy and advantage with such embodiments is to secure and control a catheter inserted directly within the urethra with the options of fully inserted into the bladder for drainage and/or partially retracted from the bladder for non-drainage, e.g., when a Foley-type balloon is not utilized within the bladder. Eliminating the need for use of the Foley-type balloon within the bladder can often eliminate a source of great discomfort, and in some instances periods of extreme pain to the patient can occur.

Equally important to the comfort of the patient using a catheter is that the device 10b may provide for a point of mechanical strain-relief on the patient 60 between the urethra and the distal end of a catheter tube 20a. The device 10b can provide for a relative degree of limited yet free rotation or swing pivoting of the catheter tube and therefore provide a desired amount of essential free movement of the catheter 20a at its point of strain-relief attachment. The device 10b may also provide for and optionally allow either flow or no-flow control (pinch valve) of the catheter tube 20a apart from selectively inserting the catheter 20a into the bladder and retracting or partially retracting the catheter 20a from the bladder. A typical and separate catheter pinch valve (not presently shown within any of the figures or embodiments), when engaged, applies a constricting force to the catheter tube, temporarily inhibiting or preventing flow of liquid through the catheter. The device 10b provides preferred compatibility with most existing commercially available pinch valves, straight catheters and various flexible medical tubing diameters currently available.

The device 10, 10c shown in FIGS. 11-15 provides a similar function, but with a formed retainer 50, 50c that is formed to correspond to the shape of the Y-junction so as to retain the catheter tube 20a thereat without pinching the catheter tube 20a, while providing enhanced securement of the catheter tube at the patient. Here, one branch of the Y-junction terminates near the formed retainer 50, 50c, facilitating locating and/or accessing the branch, e.g., for inflating or deflating the balloon of a Foley-type catheter.

The device 10, 10d shown in FIGS. 16-22 provides a similar function, but with a formed retainer 50, 50d that is formed to correspond to the shape of the three tube junction of a catheter 20, 20b so as to retain the tubes thereat without pinching the tube. Similarly, the device 10, 10e shown in FIGS. 23-25 provides a similar function, but with a box-type retainer 50, 50e that retains the three tubes of the catheter 20, 20*b* thereat in a similar manner as discussed above with respect to the embodiments of FIGS. 1-10.

Figure 26:
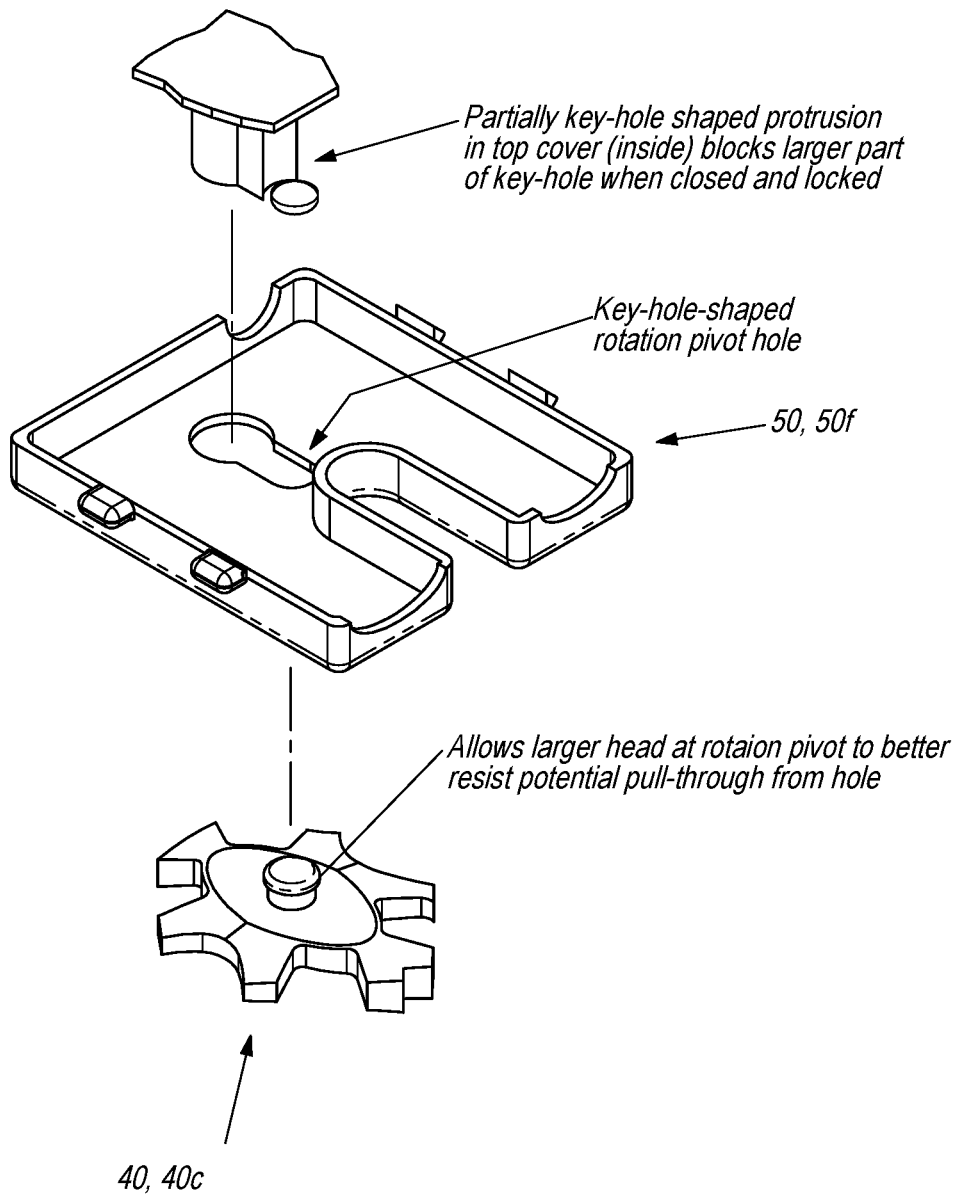
FIG. 26 is an exploded perspective view of another device in accordance with the present invention.
Figure 32A:
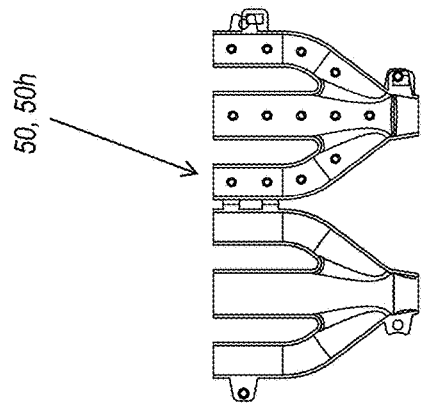
FIGS. 32A-C are plan views of a retainer, shown in its open state, of the device of FIGS. 30A-C.
Figure 32B:
Figure 32C:
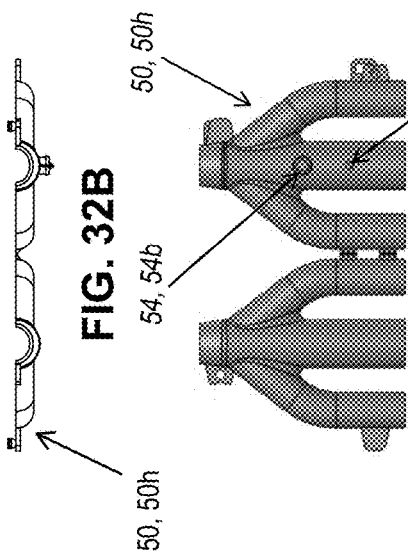
Figure 30A:
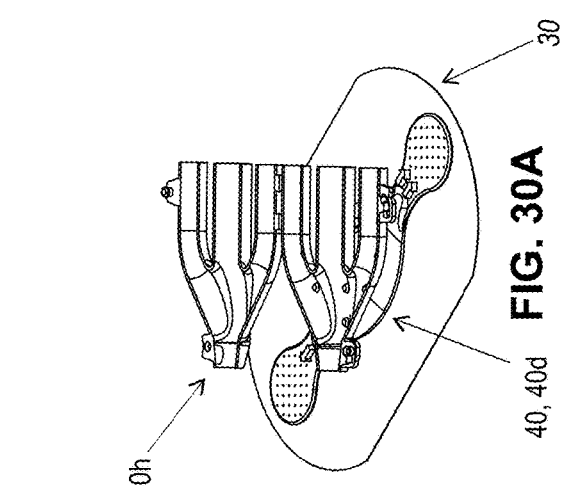
FIGS. 30A-C are perspective and plan views of another device in accordance with the present invention.
Figure 31A:
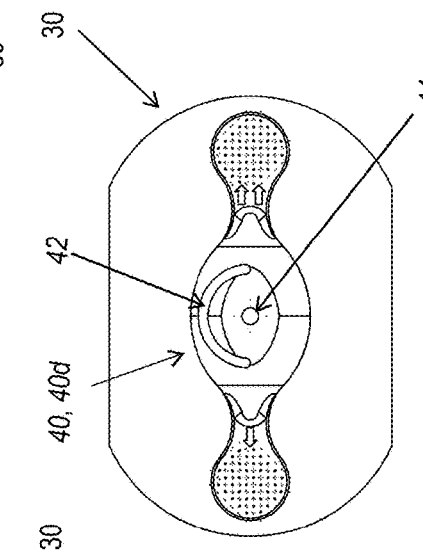
FIGS. 31A and 31B are plan views of a base and a skin adhesive patch of the device of FIGS. 30A-C.
Figure 31B:
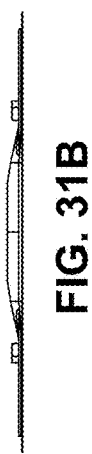
Figure 30B:
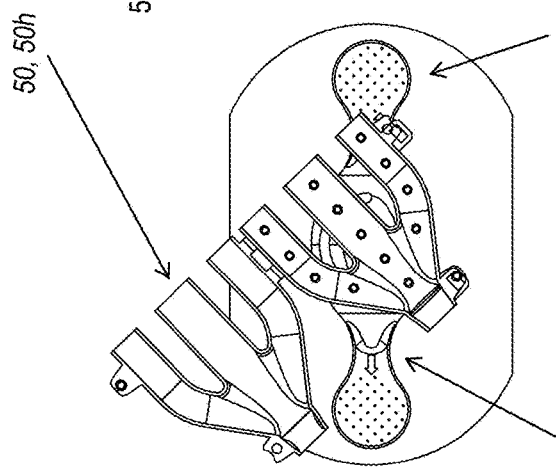
Figure 30C:
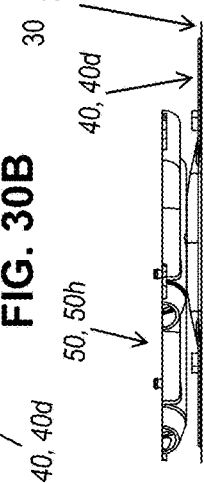
Figure 33A:
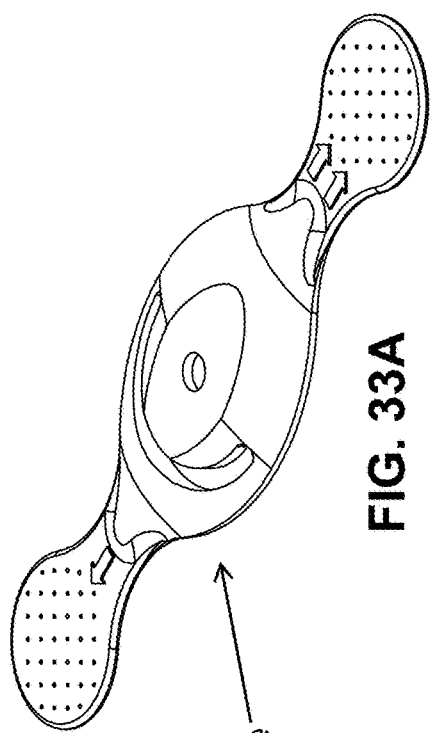
FIGS. 33A-D are perspective, plan, and close-up views of a base of another device in accordance with the present invention.
Figure 33D:
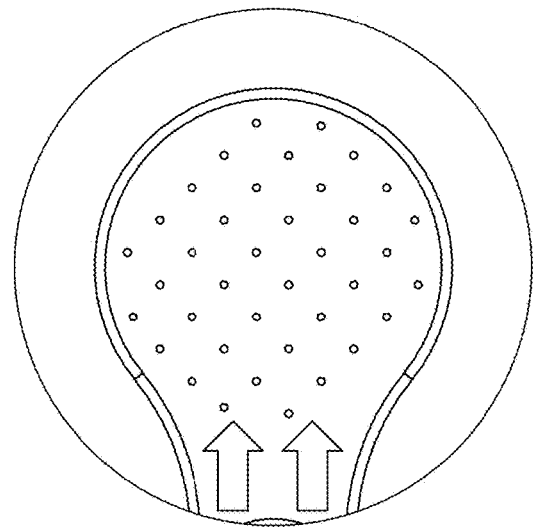
Figure 33B:
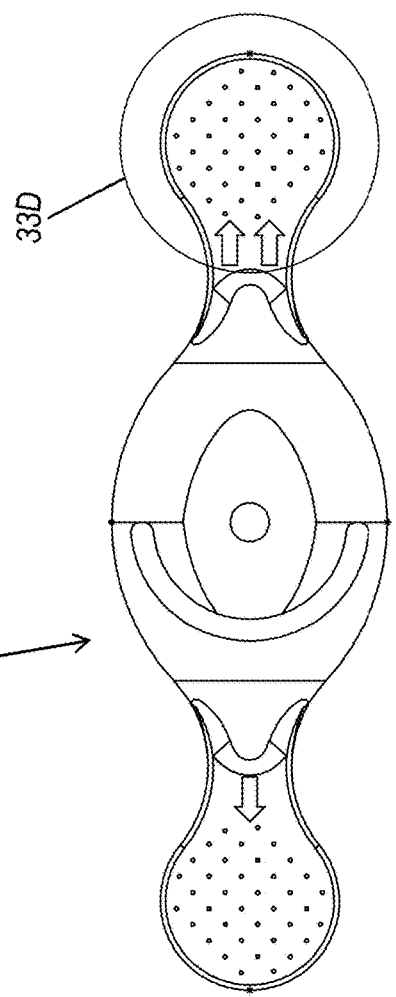
Figure 33C:
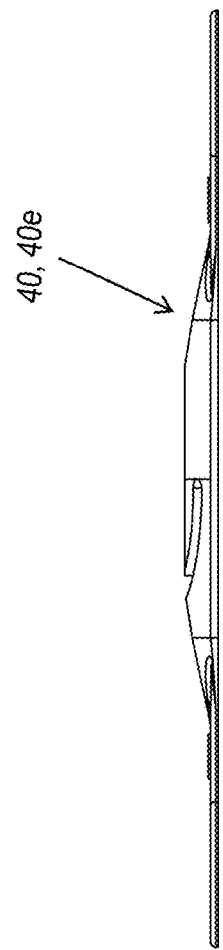
Figure 34:
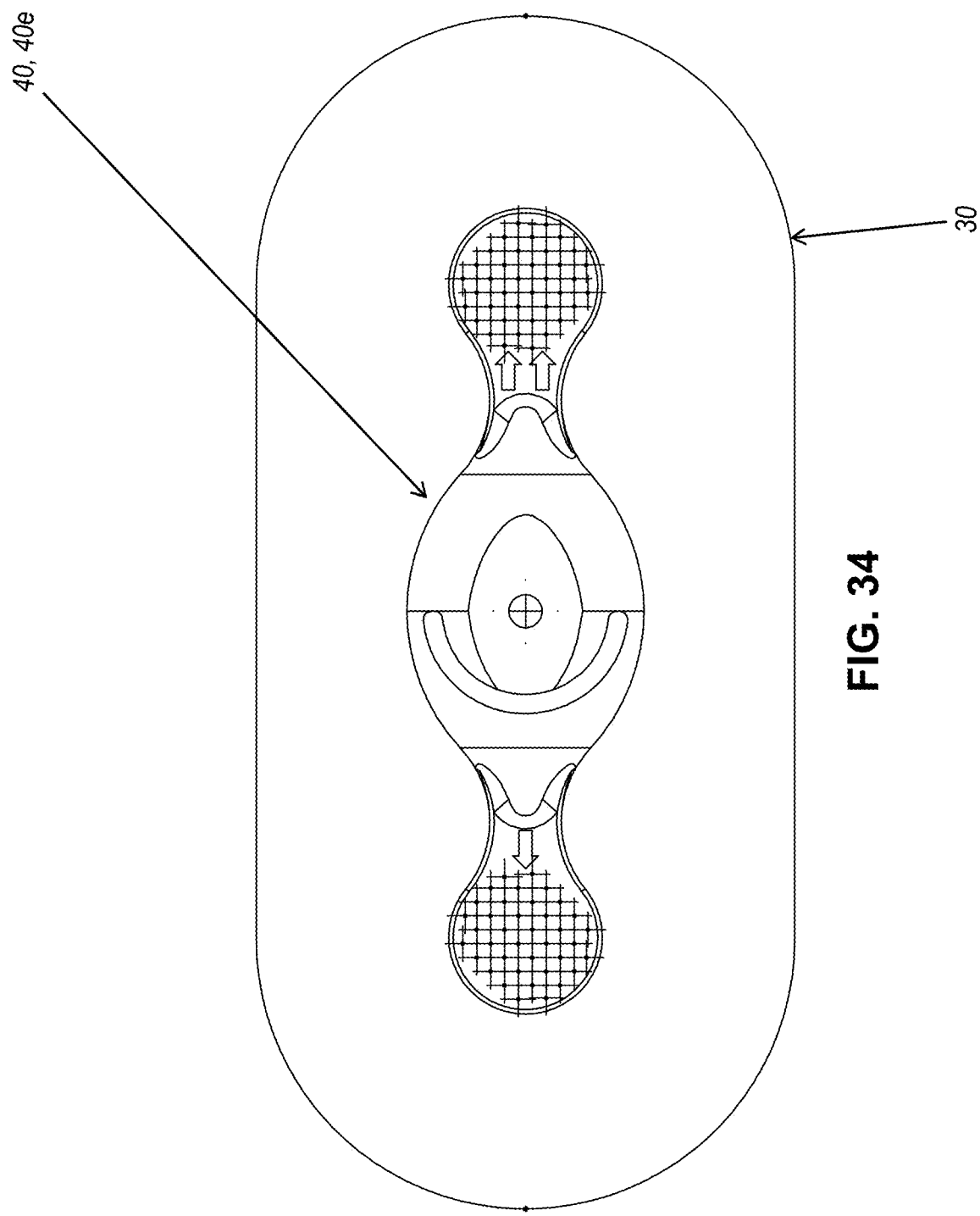
FIG. 34 is a plan view of the base and a skin adhesive patch of FIGS. 33A-D.
Figures 35, 36A, 36B:
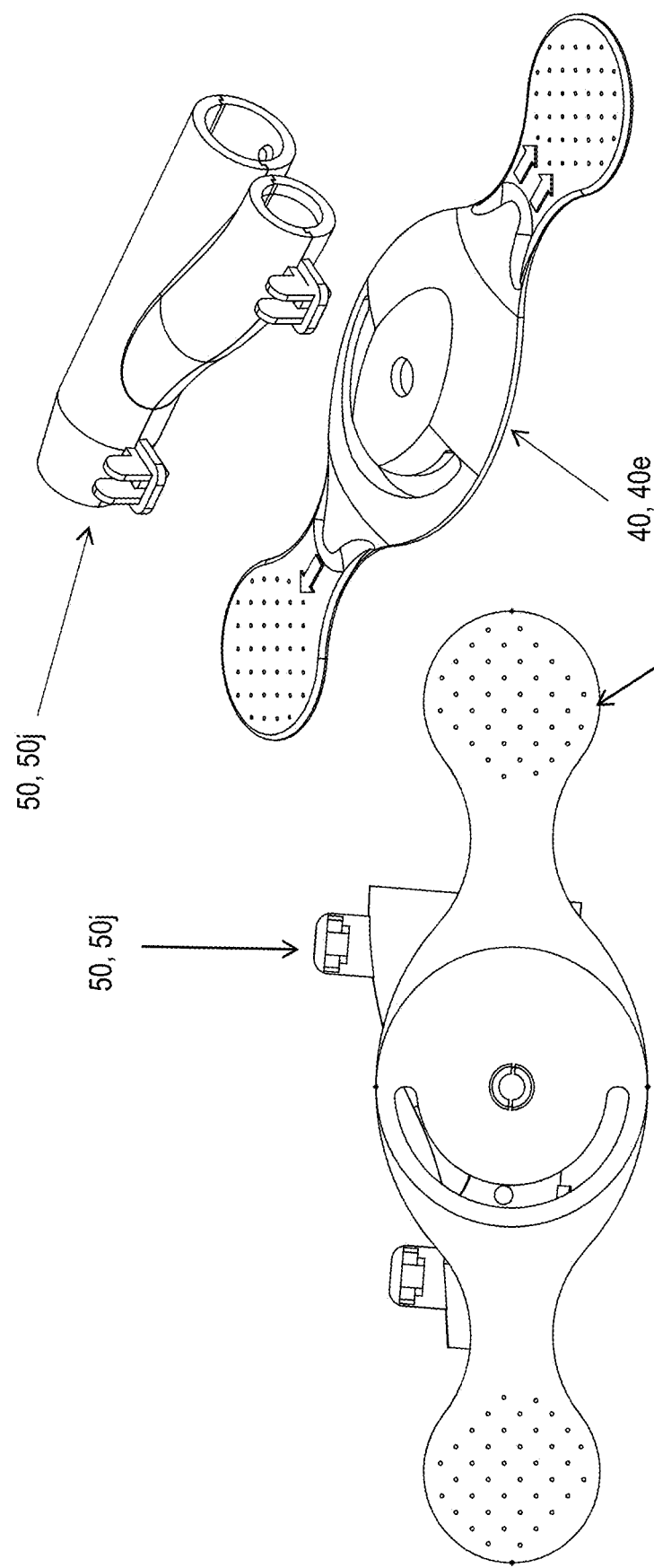
FIG. 35 is an exploded perspective view of the device including a retainer and the base of FIGS. 33A-D.
FIGS. 36A and 36B are underside plan and side views of the device of FIG. 35.
Figure 38:
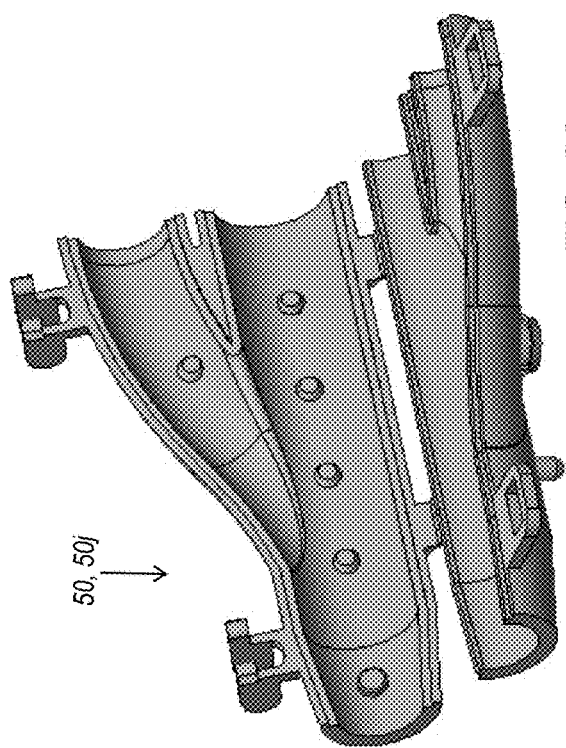
FIG. 38 is a perspective view of a retainer, suitable for the devices of FIGS. 35 and 37A-B, shown in its open state.
Figure 39C:
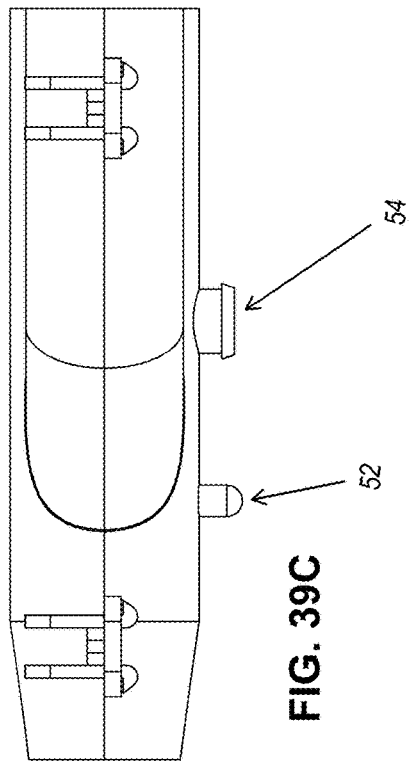
FIGS. 39A-C are plan and side views of the retainer of FIG. 38, shown in its closed state.
Figure 39A:
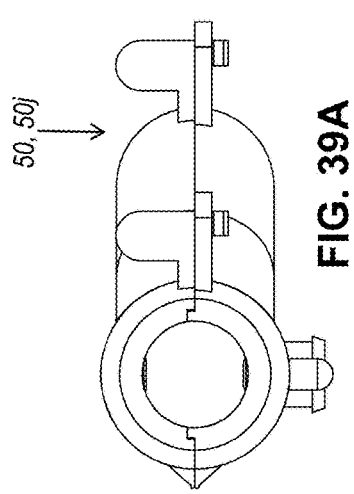
Figure 39B:
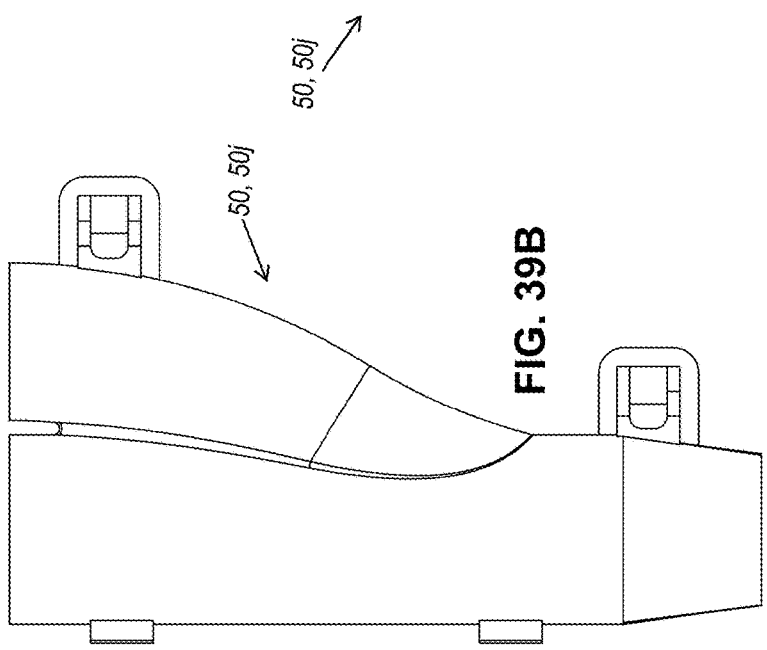

The device 10, 10*f* of FIG. 26 provides an alternate "key-hole design" at the rotation hole in the base 40, 40*c* of the retainer 50, 50*f*. A partially key-hole-shaped (or other suitably-shaped) protrusion may be provided at the top cover (inside), and may block a larger part of the key-hole (at the bottom cover of the retainer) when closed. The larger part of the key-hole may be substantially circular in shape and have a sufficiently large diameter to allow the head of the pivot pin to pass through. The smaller part of the key-hole may be substantially narrower than the head of the pivot pin while being sufficiently wide to accommodate the shaft of the pivot pin. Thus, the retainer may be attached to the base by passing the head of the pivot pin through the larger part of the key-hole, then repositioning the retainer with respect to the base so that the shaft of the pivot pin is positioned in the smaller part of the key-hole. The retainer, when closed, may maintain the position of the shaft of the pivot pin in the smaller part of the key-hole, blocking or preventing the head of the pivot pin from passing through the larger part of the key-hole. For example, this retainer allows for use of a larger head at the end of the pivot pin to better resist potential pull-through from the hole in the retainer 50*f*. This feature may further allow for easier removal and replacement of the retainer 50*f* at the pivot mounting for inspection and cleaning the pivot or inspection and optional replacement of the retainer 50*f* by simply opening the top cover and disengaging the pivot pin from the key-hole opening in the retainer. This feature may also provide for interchange of optional retainers for alternate applications without having to necessarily remove and replace the base, the catheter or the adhesive skin patch. Therefore, such a design feature can provide the advantage of ease of maintenance and convenience to both the patient and medical staff, and may further promote potential reductions in medical staff time and patient service costs within a medical facility.

The device 10, 10*g* shown in FIGS. 27A-29B provides a similar function as the embodiments set forth above and shown in FIGS. 1-25, but with a base 40, 40*d* having an arcuate slot 42 extending approximately 180 degrees around the pivot axis at the rotation hole of the base 40*d* and a retainer 50, 50*g* having a guide pin 52, 52*a* that protrudes from the retainer 50, 50*g* at a distance from the pivot axis and that slidably or movably engages the slot. The arcuate slot may extend entirely or partially through the base. That is, the slot may be a notch etched or otherwise formed into the surface of the base to a sufficient depth to maintain the guide pin in the slot as the base rotates. Optionally, the guide pin may be spring loaded, with the spring exerting a force, e.g., along the longitudinal axis of the guide pin, to engage and/or maintain the guide pin in the slot. The guide pin may slide or move along the length of the slot as the retainer 50*g* rotates relative to the base 40*d* via a rotational/pivot pin 54, 54*a* on the retainer 50, 50*g* rotatably engaged with a hole 44 near a center of the base 40*d*. The length of the slot may limit or set the extent to which the retainer 50*g* rotates, e.g., the retainer 50*g* is prohibited from rotating when the guide pin abuts an end of the slot. Optionally, the slot may be any shape that allows for arcuate movement of the guide pin and that limits or sets the extent to which the retainer 50*g* rotates. For example, the slot may be a substantially circular or semi-circular opening or notch in the base. The substantially circular or semi-circular opening or notch may have stops or ends that limit motion of the guide pin to the range between the stops. For example, the stops may be positioned approximately 180 degrees apart, protruding inwardly from the edge of the substantially circular opening or notch, thus limiting motion of the guide pin to the range between the stops.

As shown in FIG. 28A, the slot may be disposed on one side of the base 40*d*, i.e., along a length of the base 40*d*. For example, if the device 10*g* were to be adhered to the patient's skin on a right leg or a left leg of the patient 60, the base 40*d* would be oriented such that the slot faces away from a center of the patient's body. That is, the orientation of the base 40*d* on a right leg may be opposite, or upside down relative to, the orientation of the base 40*d* on a left leg. The retainer thus may pivot about 180 degrees with the pivoting having the upper end of the retainer facing upward (when the guide pin is at the upper end of the slot) or downward (when the guide pin is at the lower end of the slot) or inward toward the center of the patient's body (as the guide pin moves along the slot between the upper and lower ends). Thus, the device provides controlled or limited pivoting of the retainer to allow for limited movement of the catheter tubing within a restricted range. The limited range of pivotal motion may inhibit and prevent kinking or twisting of the catheter tubes as the patient remains at rest or moves. Furthermore, the limited range of pivotal motion may further facilitate locating and/or accessing and servicing a branch of the catheter tube terminating near the retainer, e.g., the inflation port of a Foley-type catheter.

The device 10, 10*h* shown in FIGS. 30A-32C provides a similar function as the embodiment shown in FIGS. 27A-29B, but with a formed retainer 50, 50*h* that is formed to correspond to the shape of the three-tube or 3-way catheter junction so as to retain the tubes thereat without pinching the tube.

The device 10, 10*j* shown in FIGS. 33A-39C provides a similar function as the embodiment shown in FIGS. 27A-29B, but with a base 40, 40*e* having a slot disposed on a different side of the base 40*e*, e.g., along a width of the upper part of the base. Similarly, the retainer 50, 50*j* may include a guide pin slidably or movably engaged with the slot, and the guide pin may slide or move along the length of the slot as the retainer 50*j* rotates relative to the base 40*e*. The retainer thus may pivot about 180 degrees with the pivoting having the upper end of the retainer facing inward toward the center of the patient's body (when the guide pin is at the respective side end of the slot) or outward away from the center of the patient's body (when the guide pin is at the opposite side end of the slot) or upward (as the guide pin moves along the slot between the opposite side ends). Thus, the device provides controlled or limited pivoting of the retainer to allow for limited movement of the catheter tubing within a restricted range. Optionally, the slot may be disposed elsewhere on the base and/or may limit the extent to which the retainer 50*j* rotates relative to the base 40*e* to a range of less than 180 degrees (or optionally a range greater than 180 degrees but less than 360 degrees).

Figure 40:
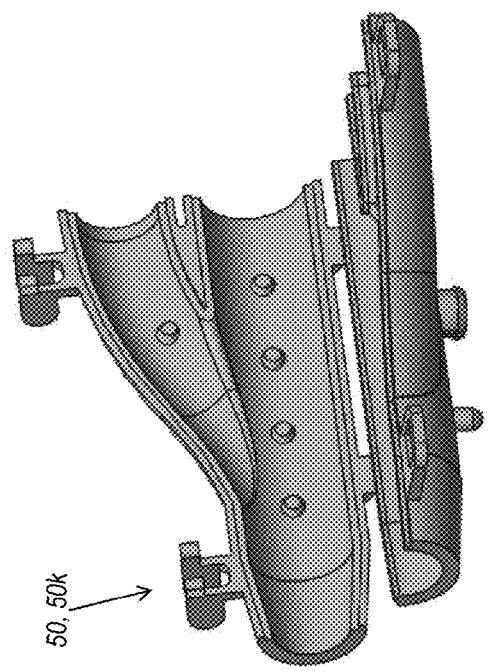
FIG. 40 is a perspective view of another retainer, similar to the devices of FIGS. 35, 37A-B and 38, shown in its open state.
Figure 41C:
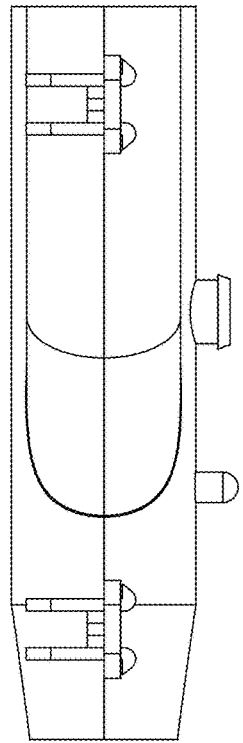
FIGS. 41A-C are plan and side views of the retainer of FIG. 40, shown in its closed state.
Figure 41A:
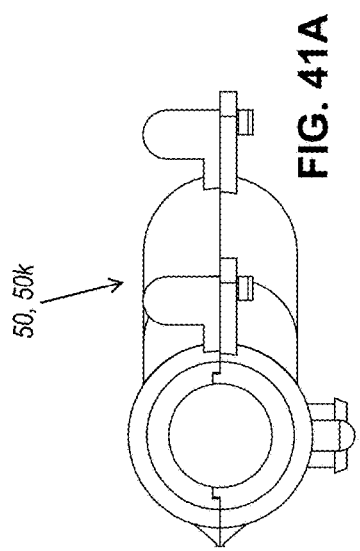
Figure 41B:
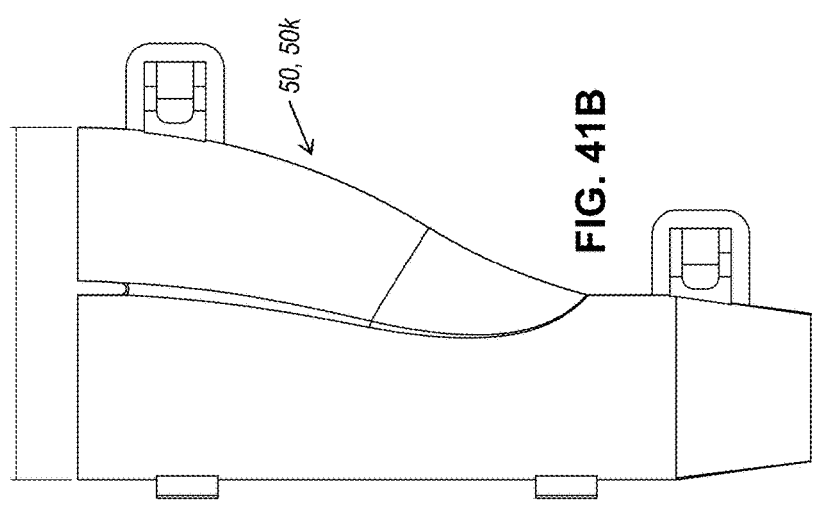
Figure 45:
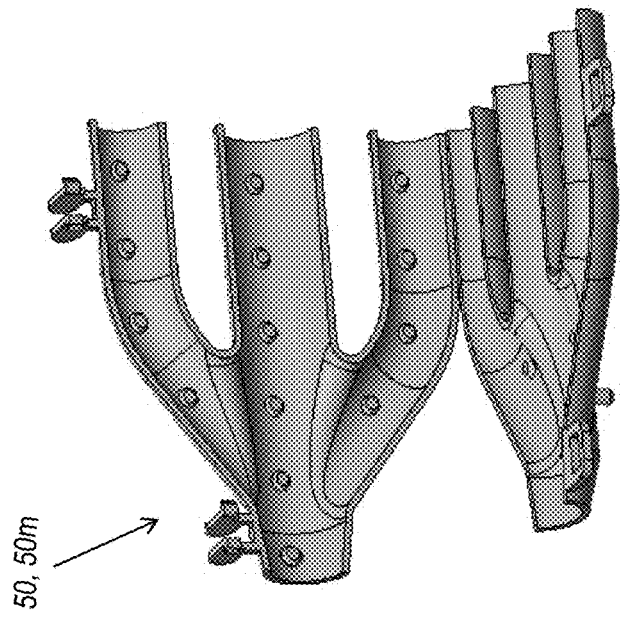
FIG. 45 is a perspective view of the retainer of the device of FIG. 42, shown in its open state.
Figure 46A:
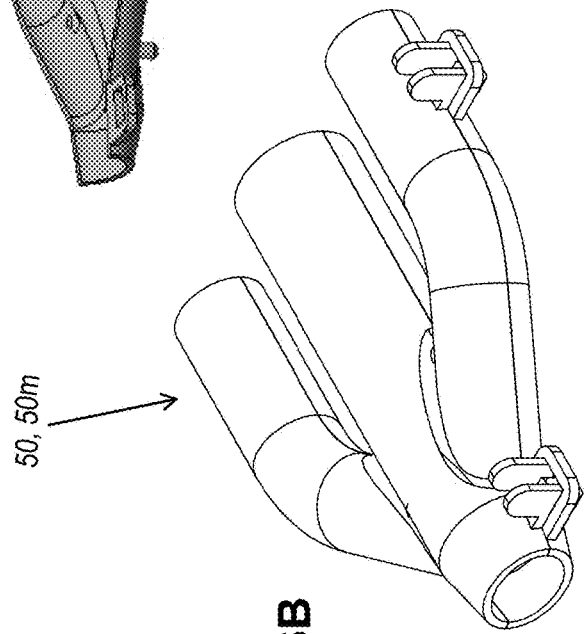
FIGS. 46A-C are perspective and plan and side views of the retainer of FIG. 45, shown in its closed state.
Figure 46B:
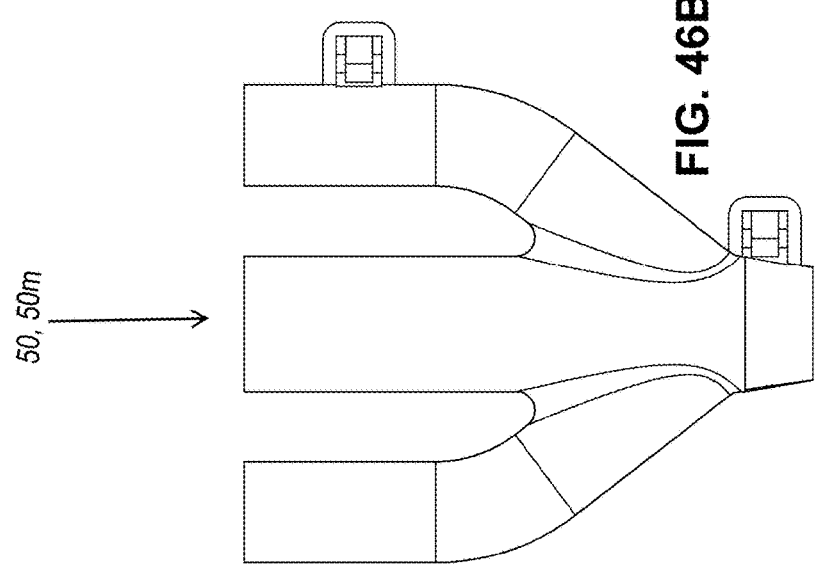
Figure 46C:
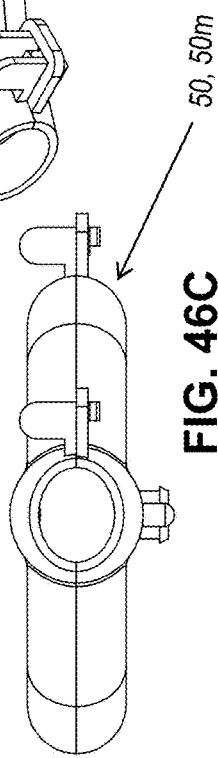
Figure 47:
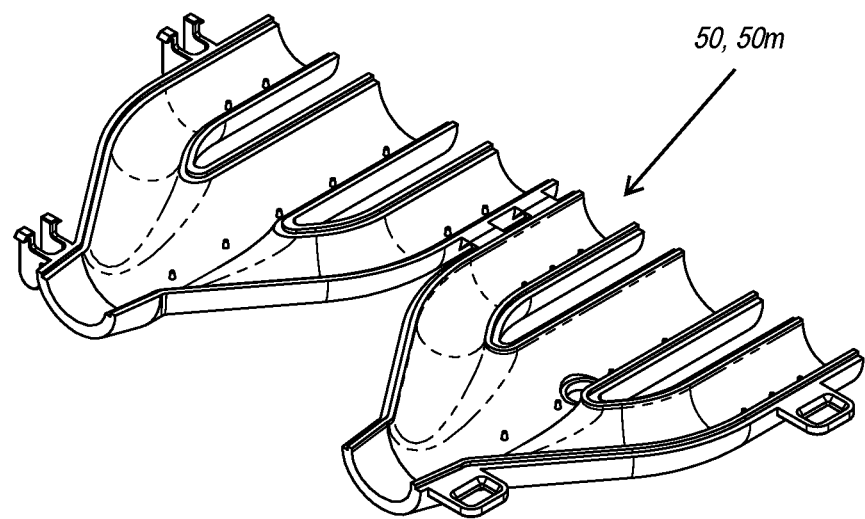
FIGS. 47 and 48 are perspective views of another retainer, shown in its open state, with a pivot aperture formed therethrough.
Figure 48:
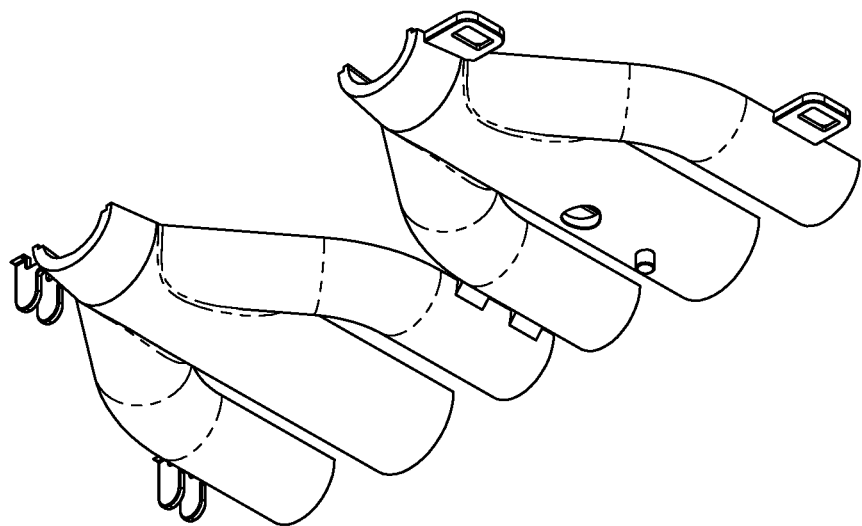
Figure 49:
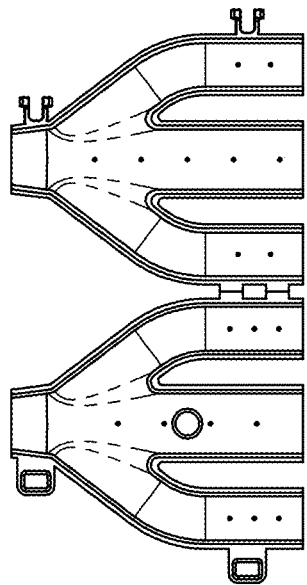
FIGS. 49 and 50 are plan views of the retainer of FIGS. 47 and 48.
Figure 50:
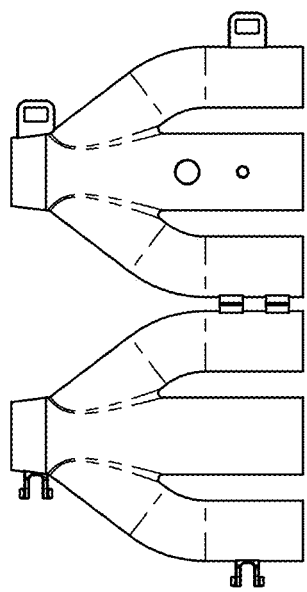
Figure 51:
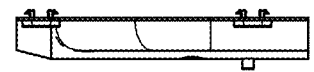
FIGS. 51-53 are side and end elevations of the retainer of FIGS. 47 and 48.
Figure 52:
Figure 53:
Figure 54:
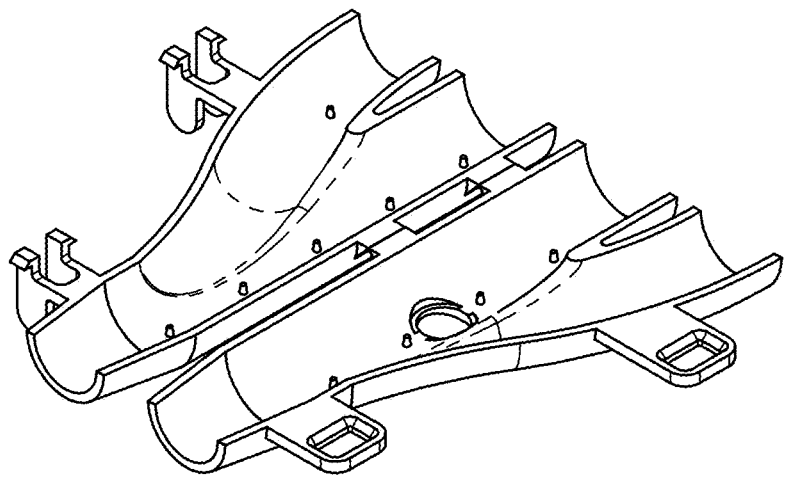
FIGS. 54 and 55 are perspective views of another retainer, shown in its open state, with a pivot aperture formed therethrough.
Figure 55:
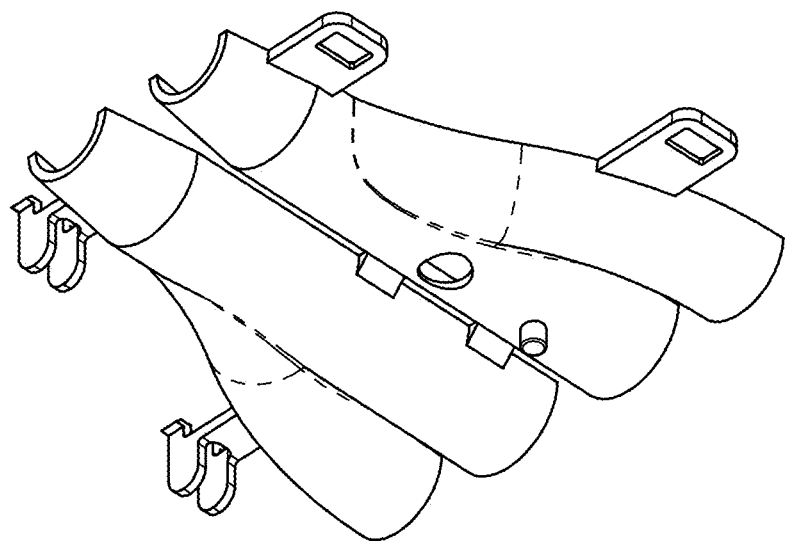
Figure 63:
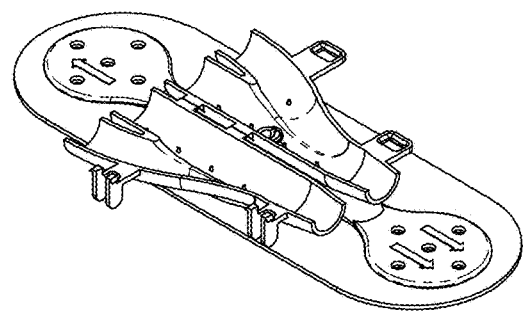
FIGS. 63 and 64 are perspective views of the assembled device.
Figure 64:
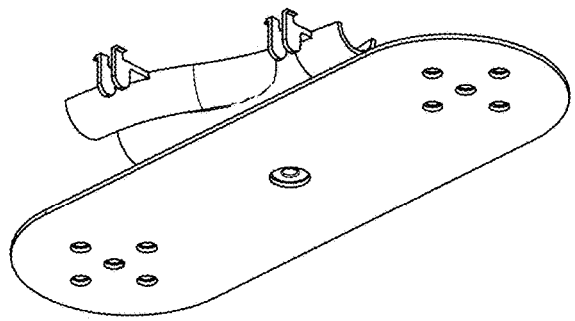
Figure 61:
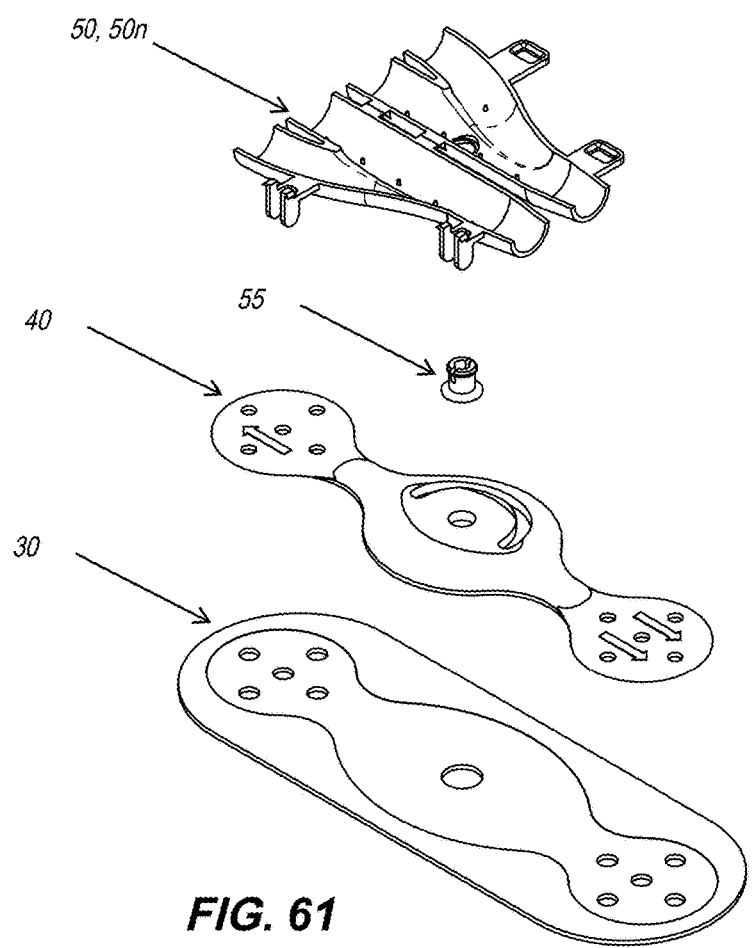
FIG. 61 is an exploded perspective view of the device, showing the retainer and base portion and a pivot element for pivotally mounting the retainer at the base element.
Figure 62:
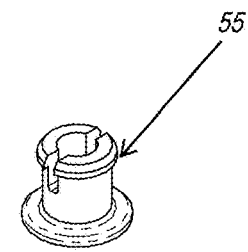
FIG. 62 is an enlarged perspective view of the pivot element.

The device 10, 10*k*, including the retainer 50, 50*k*, shown in FIGS. 40-41C provides a similar function as the embodiment shown in FIGS. 27A-29B, such that a detailed discussion of the devices need not be repeated herein. The retainers 50, 50*j* and 50, 50*k* are pivotally attached at the base via a pivot pin protruding from the retainer and received through an aperture in the base, and the retainer includes the guide pin that is movably disposed at the arcuate slot or the like that limits the pivotal range of movement of the retainer at the base, such as in a similar manner as described above. Alternatively, the retainer retainers may be pivotally attached at the base via a pin protruding from the base and received through an aperture in the retainer (see FIGS. 54-60). The device, including the retainer, shown in FIGS.

54-60 provides a similar function as the embodiments shown in FIGS. 33A-41C, such that a detailed discussion of the devices need not be repeated herein.

The device 10, 10m shown in FIGS. 42-46C provides a similar function as the embodiment shown in FIGS. 33A-41C, but with a formed retainer 50, 50m that is formed to correspond to the shape of the three-tube junction so as to retain the tubes thereat without pinching the tube. The retainer 50, 50m is pivotally attached at a base via a pivot pin protruding from the retainer and received through an aperture in the base, and the retainer includes a guide pin that is movably disposed at an arcuate slot or the like that limits the pivotal range of movement of the retainer at the base, such as in a similar manner as described above. Alternatively, the retainer 50, 50m may be pivotally attached at the base via a pin protruding from the base and received through an aperture in the retainer (see FIGS. 47-53). The device 10, 10m, including the retainer 50, 50m, shown in FIGS. 42-46C provides a similar function as the embodiment shown in FIGS. 33A-41C, such that a detailed discussion of the devices need not be repeated herein.

Optionally, and such as shown in FIGS. 61-64, a device, including a retainer 50, 50n and base portion, has a separate pivot element 55 (FIGS. 61 and 62) that may snap into an aperture in the base and may snap into an aperture in the retainer to pivotally mount the retainer at the base element. For example, the pivot element may be inserted through the aperture in the base, with a wider end or flange of the pivot element engaging an underside of the base, and may be snapped into the aperture of the retainer (with the end of the pivot element having slots to allow for inward flexing at the end for inserting the end into the aperture of the retainer). Alternatively, the separate pivot element 55 may be inserted through the aperture in the retainer to engage or snap attach to the base. In the illustrated embodiment of FIGS. 61-64, the retainer comprises a two-tube junction shape, but may be shaped or formed to correspond to, e.g., the shape of the three-tube junction so as to retain the tubes thereat without pinching the tube. The device, including the retainer, shown in FIGS. 61-64, provides a similar function as the embodiments shown in FIGS. 33A-60, such that a detailed discussion of the devices need not be repeated herein.

Thus, an adhesive patch 30 may be adhesively attached at a patient's skin (such as via a suitable skin-safe adhesive disposed at the underside of the patch that adheres the patch to the patient's skin and that allows for safe removal of the patch from the patient's skin) and the base 40 may be attached at the patch (such as by adhesively attaching the base at the patch). The location of the base at the patch may be set by the patch being received at a slight recess (that may correspond to the shape or profile of the patch) at the upper surface of the adhesive patch, such that the aperture(s) through the base generally align with apertures through the patch. The pivot element may be inserted through the center aperture of the base before the base is attached at the patch and/or before the patch is attached to the patient, with a center hole of the patch and/or the thickness dimension of the base providing space or clearance for the base flange of the pivot element so that the pivot element is spaced from the patient's skin when the patch is adhered to the patient. The retainer (such as a two-tube or three-tube retainer) may then be selected (e.g., selection of a retainer having the appropriate style and size for the particular catheter tube or tubes that are to be retained) and snapped to the pivot element, and the catheter tubes may then be routed through the retainer (when the retainer is open), whereby the retainer is snapped closed to retain the tubes at the device, while allowing limited rotation or pivotal movement of the retainer and tubes relative to the base and adhesive patch at the patient.

Therefore, the device of the present invention provides for pivotable or adjustable attachment of the catheter tube at the patient, so that, when the patient moves, the device can pivot to limit or substantially preclude pulling, binding or potential pinching of the catheter tube. The device may utilize aspects of the external catheter stabilizer devices described in U.S. Pat. No. 10,086,168, which is hereby incorporated herein by reference in its entirety. Optionally, the device described herein may be used in conjunction with the device of U.S. Pat. No. 10,086,168, with the device of U.S. Pat. No. 10,086,168 being disposed at a surgically created opening in the body, or for example, a stoma opening with respect to a bladder, and guiding the tube from there, and with the device 10 described herein pivotally attaching at the patient's leg (or optionally, any preferred remote location from a surgically created opening or stoma) to both guide the drainage tube and limit the preferred range of free pivotal movement of the tube as it extends toward the bodily fluid collection bag or container.

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:

1. An external catheter stabilizer device for stabilizing and retaining a catheter tube, said external catheter stabilizer device comprising:
   a base portion configured to adhesively attach at a patient;
   a retaining element configured to retain the catheter tube thereat;
   a pivot element that pivotally attaches the retaining element to the base portion so as to allow for pivotal movement of the retaining element about a pivot axis generally normal to the patient where the base portion is attached;
   wherein the retaining element comprises a guide pin protruding therefrom and spaced from the pivot element;
   wherein the pivotal movement of the retaining element relative to the base portion is limited to a selected range via engagement of the guide pin of the retaining element with an arcuate slot at the base portion;
   wherein the arcuate slot is disposed along a side of the base portion sideward of the pivot axis when the base portion is attached at the patient; and
   wherein the arcuate slot extends 180 degrees about the pivot axis, limiting pivotal movement of the retaining element relative to the base portion to 180 degrees to facilitate locating a branch of the catheter tube terminating near the retaining element.

2. The external catheter stabilizer device of claim 1, wherein the arcuate slot is disposed along an upper part of the base portion above adjacent to the pivot axis when the base portion is attached at the patient.

3. The external catheter stabilizer device of claim 1, wherein the retaining element comprises a housing that is openable and closable, and wherein, when the catheter tube is disposed at the housing and the housing is closed, the catheter tube is retained at the housing.

4. The external catheter stabilizer device of claim 3, wherein the catheter tube comprises a Y-shaped junction, and wherein the housing is configured to receive and retain the Y-shaped junction.

5. The external catheter stabilizer device of claim 3, wherein the catheter tube comprises a three-tube junction, and wherein the housing is configured to receive and retain the three-tube junction.

6. The external catheter stabilizer device of claim 3, wherein the housing conforms to the shape of the catheter tube at the housing.

7. The external catheter stabilizer device of claim 1, wherein the base portion is adhesively attached to an adhesive patch that is adhered to the patient's skin.

8. The external catheter stabilizer device of claim 1, wherein the pivot element detachably attaches the retaining element to the base portion.

9. The external catheter stabilizer device of claim 1, wherein the pivot element is formed as part of the retaining element and is received at an aperture of the base portion.

10. The external catheter stabilizer device of claim 1, wherein the pivot element is formed as part of the base portion and is received at an aperture of the retaining element.

11. The external catheter stabilizer device of claim 1, wherein the pivot element comprises a separate pivot element formed separate from the retaining element and the base portion and is received at an aperture of the base portion and at an aperture of the retaining element.

12. An external catheter stabilizer device for stabilizing and retaining a catheter tube, said external catheter stabilizer device comprising:
   a base portion configured to adhesively attach at a patient;
   a retaining element configured to retain the catheter tube thereat;
   a pivot element that pivotally attaches the retaining element to the base portion so as to allow for pivotal movement of the retaining element about a pivot axis generally normal to the patient where the base portion is attached, wherein the pivot element detachably attaches the retaining element to the base portion;
   wherein the base portion includes an arcuate slot that is disposed along a side of the base portion sideward of the pivot axis when the base portion is attached at the patient; and
   wherein the arcuate slot extends 180 degrees about the pivot axis, limiting pivotal movement of the retaining element relative to the base portion to 180 degrees to facilitate locating a branch of the catheter tube terminating near the retaining element.

13. The external catheter stabilizer device of claim 12, wherein the retaining element further comprises a housing that is openable and closable, and wherein, when the catheter tube is disposed at the housing and the housing is closed, the catheter tube is retained at the housing.

14. The external catheter stabilizer device of claim 13, wherein the housing is configured to permit detaching the retaining element from the base portion when the housing is open, and wherein the housing is configured to prevent detaching the retaining element from the base portion when the housing is closed.

15. The external catheter stabilizer device of claim 14, wherein the pivot element comprises a shaft and a head at an end of the shaft, a diameter of the head being greater than a diameter of the shaft, and wherein the housing comprises a rotation hole comprising a wider portion and a narrower portion, the wider portion configured to permit passage of the head of the pivot element, the narrower portion configured to permit passage of the shaft of the pivot element and to resist passage of the head of the pivot element, and wherein, when the shaft of the pivot element is disposed in the narrower portion of the rotation hole, the housing is configured to maintain the shaft of the pivot element in the narrow portion of the rotation hole while the housing is closed.

16. The external catheter stabilizer device of claim 12, wherein the pivot element is formed as part of the retaining element and is received at an aperture of the base portion.

17. The external catheter stabilizer device of claim 12, wherein the pivot element is formed as part of the base portion and is received at an aperture of the retaining element.

18. The external catheter stabilizer device of claim 12, wherein the pivot element comprises a separate pivot element formed separate from the retaining element and the base portion and is received at an aperture of the base portion and at an aperture of the retaining element.

* * * * *

UNITED STATES PATENT AND TRADEMARK OFFICE
CERTIFICATE OF CORRECTION

PATENT NO. : 11,364,366 B2
APPLICATION NO. : 16/722700
DATED : June 21, 2022
INVENTOR(S) : Sarah L. Olson et al.

It is certified that error appears in the above-identified patent and that said Letters Patent is hereby corrected as shown below:

In the Claims

Column 10
Line 61, Claim 2, "portion above adjacent" should be --portion adjacent--

Signed and Sealed this
Nineteenth Day of July, 2022

Katherine Kelly Vidal
*Director of the United States Patent and Trademark Office*